(12) United States Patent
Godin

(10) Patent No.: US 8,556,934 B2
(45) Date of Patent: Oct. 15, 2013

(54) ARTICLE, SYSTEM, AND METHOD FOR SECURING MEDICAL DEVICES TO TREAT OBESITY, GASTRO-ESOPHAGEAL REFLUX DISEASE (GERD) AND IRRITABLE BOWEL SYNDROME (IBS) REVERSIBLY

(76) Inventor: Norman Godin, Geneva (CH)

( * ) Notice: Subject to any disclaimer, the term of this patent is extended or adjusted under 35 U.S.C. 154(b) by 1374 days.

(21) Appl. No.: 11/751,260

(22) Filed: May 21, 2007

(65) Prior Publication Data

US 2008/0228030 A1 Sep. 18, 2008

Related U.S. Application Data

(60) Provisional application No. 60/747,712, filed on May 19, 2006, provisional application No. 60/884,770, filed on Jan. 12, 2007.

(51) Int. Cl.
*A61B 17/08* (2006.01)

(52) U.S. Cl.
USPC ........................................... 606/219

(58) Field of Classification Search
USPC ............. 606/151, 139, 142, 75, 103, 74, 143, 606/219, 232; 227/77, 175.1, 179.1, 901, 227/902
See application file for complete search history.

(56) References Cited

U.S. PATENT DOCUMENTS

| | | | |
|---|---|---|---|
| 4,291,698 A * | 9/1981 | Fuchs et al. | 606/232 |
| 4,655,222 A * | 4/1987 | Florez et al. | 606/219 |
| 5,242,457 A | 9/1993 | Akopov et al. | |
| 5,501,683 A * | 3/1996 | Trott | 606/139 |
| 5,501,696 A * | 3/1996 | Trott | 606/232 |
| 6,026,326 A * | 2/2000 | Bardy | 607/40 |
| 6,200,330 B1 * | 3/2001 | Benderev et al. | 606/232 |
| 6,228,055 B1 * | 5/2001 | Foerster et al. | 604/116 |
| 7,326,231 B2 * | 2/2008 | Phillips et al. | 606/219 |
| 2004/0236419 A1 * | 11/2004 | Milo | 623/2.36 |
| 2004/0254608 A1 * | 12/2004 | Huitema et al. | 606/219 |

* cited by examiner

*Primary Examiner* — Gregory Anderson
(74) *Attorney, Agent, or Firm* — Michael B. Fein, Esq.; Eckert Seamans Cherin & Mellott, LLC

(57) ABSTRACT

A medical staple formed from a nitinol wire, the staple having two elongated arms which extend upwardly and outwardly from a central loop in two opposing generally semicircular courses forming an arc extending upwardly and outwardly and an end second comprising a sharpened endpoint, the endpoint being the arms bendable under resistance, is disclosed. In some embodiments the arms extend upwardly on a parallel course and then outwardly. The material is preferably an alloy with hyperelastic characteristics. The staples are placed in a flexible endoscope and a lumen catheter within the endoscope, using a hook or forceps in the lumen catheter having a distal end in the lumen of the catheter and the staple distal to the forceps in folded configuration with the arms folded inward in the lumen catheter, positioning the distal end of the lumen catheter at a location in the patient's gastrointestinal tract where stapling is desired, moving the forceps distally so as to force the staple forward out of the lumen catheter and cause the end points to pierce the patient's inner wall of the gastrointestinal tract.

11 Claims, 22 Drawing Sheets

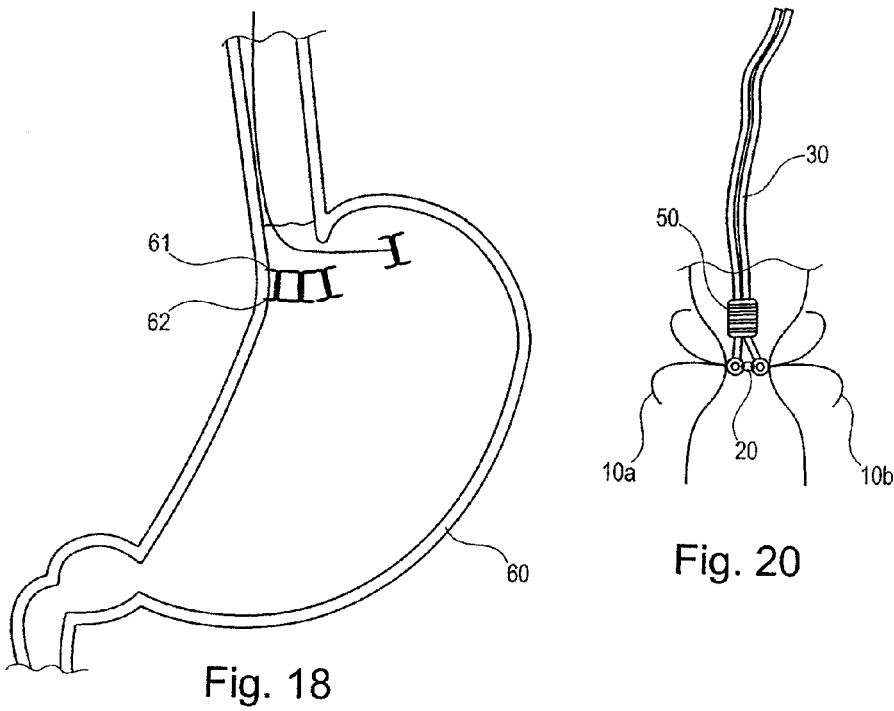
Fig. 18
Fig. 20
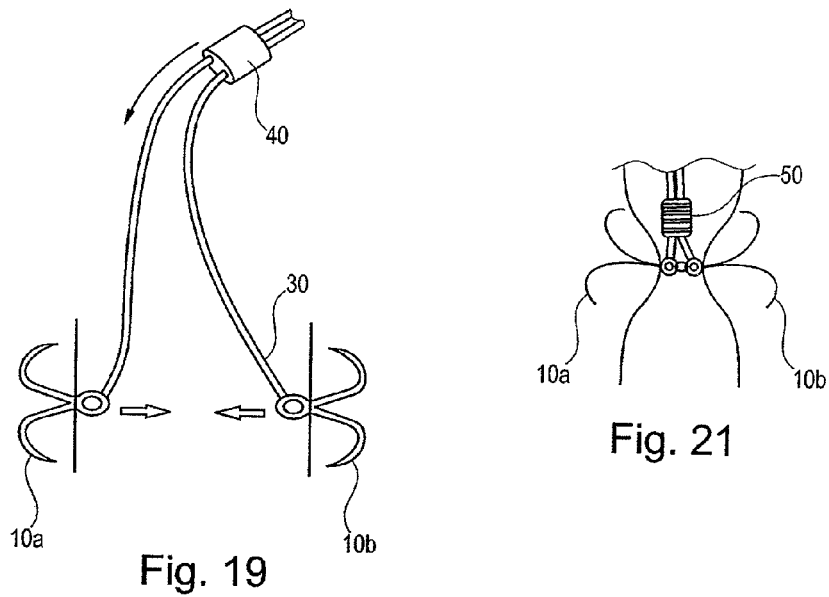
Fig. 19
Fig. 21

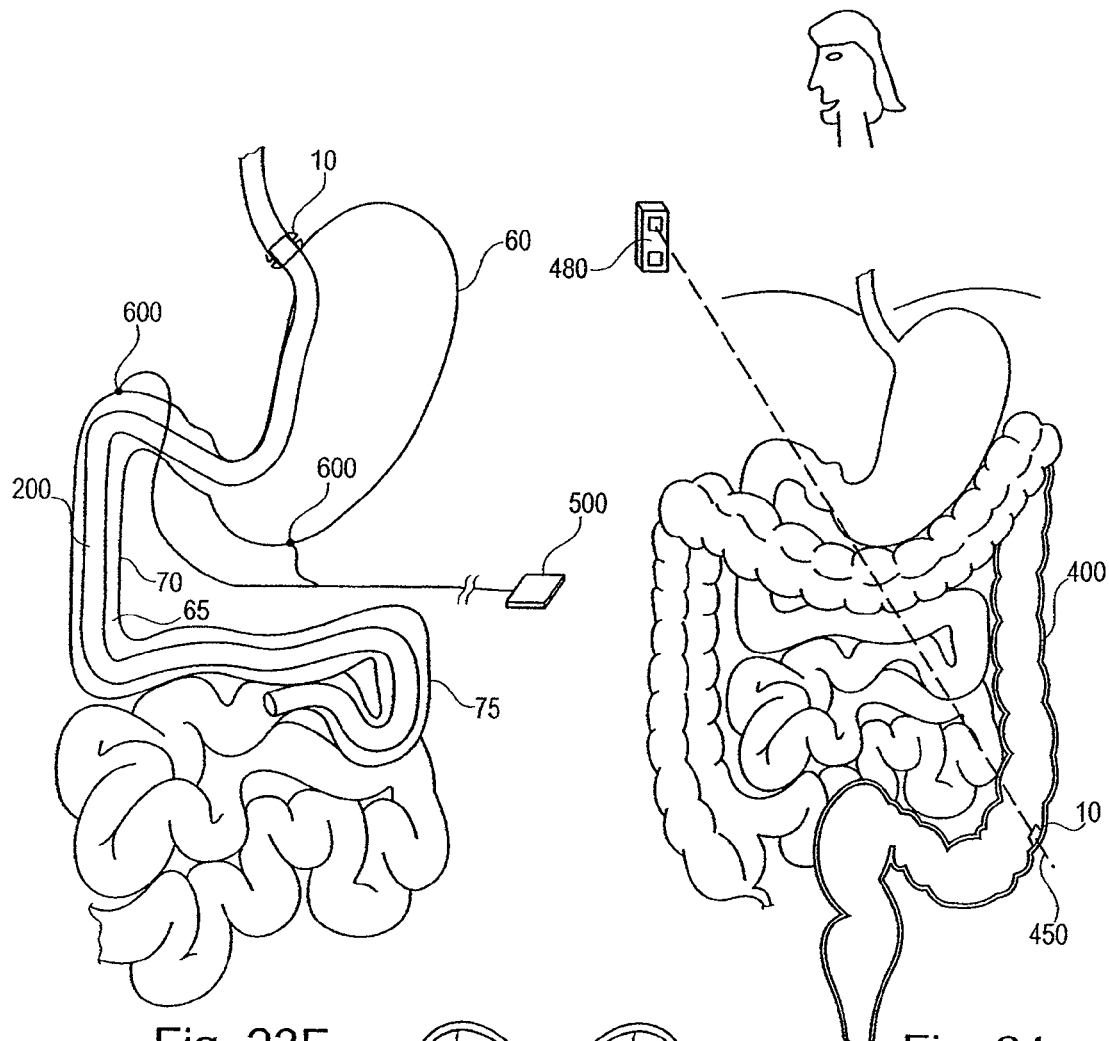
Fig. 23F
Fig. 24
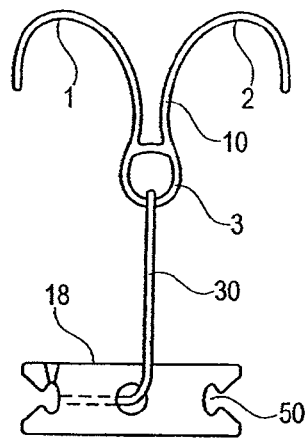
Fig. 25

ARTICLE, SYSTEM, AND METHOD FOR SECURING MEDICAL DEVICES TO TREAT OBESITY, GASTRO-ESOPHAGEAL REFLUX DISEASE (GERD) AND IRRITABLE BOWEL SYNDROME (IBS) REVERSIBLY

CROSS REFERENCE TO RELATED APPLICATION

This application claims benefit of provisional applications Ser. No. 60/747,712 filed May 19, 2006 and 60/884,770 filed Jan. 12, 2007.

BACKGROUND OF THE INVENTION

The present invention relates to the field of medicine, particularly to securing medical devices to tissue or organs, and to reversing the procedure and removing the devices.

The most common way to secure medical tissues to tissues or organs is by stapling with conventional surgical staples formed from a single length of wire in an approximate U-shape. For example, McGarry, et al., in U.S. Pat. No. 5,366,479, disclose endoscopic application of staples for attaching surgical mesh to body tissue in laparoscopic hernia surgery. In this patent, the stapler is a rigid instrument and cannot be used through the mouth into the esophagus where a flexible instrument is needed. Furthermore, the stapling system of this patent is not reversible.

For certain types of devices placed through the mouth, conventional stapling with a rigid stapler is not possible and so various alternatives using flexible instruments have been devised. For example, to treat a condition known as Gastro-Esophageal Reflux Disease (GERD), a tubular valve has been designed for letting free passage of food from the esophagus into the stomach but stopping food and gastric content such as hydrochloric acid and bile from refluxing from the stomach into the esophagus. Godin, U.S. Pat. No. 5,861,036, described a Gastro-esophageal Anti-Reflux Device (GARD) and Godin, U.S. Pat. No. 6,764,518 described a system for securing the GARD comprising a ring which could be collapsed into a smaller diameter for placement through the mouth and placed in a hiatus hernia after calibration of the diameter of the hernia with a catheter. Such ring was designed to place the GARD tubular valve in the lower esophagus or in a hiatus hernia associated with severe GERD and keep it in place for a significant amount of time, such as months and years, as severe GERD is a chronic condition.

While the aforementioned method of placing a GARD worked for some patients, it was insufficient in certain cases.

In a different approach to addressing GERD, endoluminal fundoplication surgery, a flexible endoscope was disclosed by Adams, et al., in U.S. Pat. No. 6,736,828, as being useful in endoluminal fundoplication surgery where a bonding agent is injected into tissue which forms an intussusception formed by pulling a selected portion of the esophagus into the stomach and displacing a fundus portion of the stomach towards the esophagus, placing a fastener across the intussusception for maintaining an esophageal wall and a gastric wall forming the intussusception adjacent to one another and then injecting the bonding agent to bond the intussusception. The disclosed fasteners are all symmetrical at both ends. Adams, et al., did not describe a flexible echo endoscopic procedure. The intussusception site is located by Adams, et al., by viewing the gastroesophogeal junction (GEJ) through the endoscope. The fastener is preferably made of polypropylene but can alternatively be made of a biocompatible material and can be a T-fastener. The fastener is inserted through a hypotube which first penetrates tissue of both the esophageal and gastric walls; then the T-fastener is inserted so the distal end of the T-fastener engages the gastric wall as the hypotube is retracted; and then the hypotube is further retracted into the sheath of a fastener delivery device. The proximal end of the T-fastener is pulled out of the hypotube by the tension exerted from the distal end of the T-fastener and then the proximal end seats against the inner wall of the esophagus, thereby holding the gastric wall and the esophagus together. One of the T-fasteners has a simple T-bar at each end, referred to herein as a fastener since the T-bars are normally biased in a T-configuration with respect to the longer joining portion but can be maintained in a reduced diameter configuration, with the T-bars "tilted" or compressed toward the longer joining portion, while inserted and maintained in a hypotube such as a hypodermic needle delivery device. Such fasteners are advanced through the hypotube until the distal portion exits the distal end of the hypotube delivery device and then regains its normally radially expanded position. In Adams, the T-bars when placed on both sides of the intussusception are visible on both sides with conventional endoscopes as one T-bar is on the esophageal side and the other one on the gastric fundal side. No echoendoscope is necessary and none is described. The Adams T-bars are not used to hold a device attached to the mucosa.

A system for suturing, tissue fixation, and transgastric penetration to facilitate surgery on the wall of the GI tract and adjacent hollow organs under Endoscopic Ultrasound (EUS) control was described by Fritscher-Ravens, et al., in Gastrointestinal Endoscopy, vol. 56, No. 5, 2002, pgs. 737 to 742. In this paper, one single tag is placed under EUS control through the mucosa. A free piece of thread as described in Figs. A-E on page 738 comes out of the tag and from the tip of the needle that is modified in order to let the thread come out of the needle. The free thread has then to be attached using either suturing systems or pledgets or tying knots that are not easily done or used through a flexible endoscope. Furthermore, the Fritscher-Ravens, et al., system was not described for use for securing medical devices, for example a GARD, to the gastrointestinal tract or any other organ.

A rigid rather than flexible laparoscopic surgery appliance for installing temporary plastic resorbable fasteners, for example for fixing parietal and visceral reinforcements, is described by Bailly, et al., in U.S. Pat. No. 6,779,701. Bailly, et al., teach binding nets for treatment of inguinal hernias. A plunger for forcing the catching bars to pivot is disclosed.

A self-securing suture wire with a T-shaped toggle designed for insertion into a bodily structure, tissue, or organ, delivered by a slotted needle, is disclosed by Levinson, et al., in U.S. Pat. No. 6,596,014. The toggle end portion can be made of nitinol, stainless steel, or biocompatible material. The suture is designed to be placed in a blood vessel from the outside of the vessel.

A T-bar fastener with a sharp end or point on the bar-like head portion, or T, so that the sharp end or point embeds itself in body tissue to securely anchor the T-bar head is disclosed by Richards, et al., in U.S. Pat. No. 4,669,473. A tool receives a fastener with the bar-like head positioned inside a bore of a sheath and the filament portion of the fastener extending out through a slot in the tool bore, the head making a sliding fit in the sheath.

Staples of various configurations have been suggested for unrelated surgical procedures and applications, for example for repair of arteries, Phillips, et al., US Patent Pub. 2003/0033006, disclose a device with a central section for abutment contact with the inner wall of a graft and two elongate members with distal ends for contacting the outer wall of the artery when the device is pierced through the graft and the artery. In FIGS. 7 and 8 of Phillips, et al., a device with a central loop is shown in unstressed configuration and in stressed configuration in a delivery tube.

A suture anchor was described by Gatturna, et al., U.S. Pat. No. 5,192,303 wherein a coupling member at one end and a barb on the other end are used to anchor a suture to bone.

Irnich, et al., U.S. Pat. No. 3,814,104, disclose a pacemaker electrode with an electrode tip having two crossing arms and a central loop.

It is an object of the present invention to provide a method and apparatus for esophageal and gastrointestinal stapling.

It is another object to provide an improved device for effectively securing medical devices to a patient's inner mucosa and reversibly remove the staple.

It is a further object to provide an improved apparatus for securing a GARD valve to a hiatus hernia or wall of a gastro-intestinal tract of a patient suffering from severe GERD associated with a hiatus hernia.

A still further object is to provide an improved staple for stomach stapling surgery to treat obesity and a method of reversing such stapling surgery for obesity.

It is also an object to place a manometric probe or several manometric probes in the colon to treat Irritable Bowel Syndrome (IBS).

A still further object is to use the clips to staples with a joining ring and make stomach folds in the cardia, i.e., the upper part of the stomach, to make pleats to treat mild to moderate GERD.

A still further object is to use the staples to create a small reservoir in the upper part of the stomach to create a restrictive pouch in the stomach to treat moderate obesity, creating a reversible endoscopic vertical banding gastroplasty.

It is a further object to use pairs of staples to create a horizontal line of stapling creating a small gastric cavity at the top of the stomach, at the cardia, mimicking endoscopically the gastric pouch obtained by the laparoscopic banding (LAP-BAND) operations for obesity.

It is a further object to provide an improved device for effectively securing restrictive and bypass tubes to treat obesity, called OB tubes as described in PCT/US06/35568.

SUMMARY OF THE INVENTION

These objects, and others which will become apparent from the following disclosure, are achieved by the present invention which in one aspect comprises a gull shaped staple having two wings and a central loop, the staple formed from a single length of flexible, resilient metal alloy wire. The wings may be folded inward for insertion in a catheter of the type used for flexible endoscopy. The staple may be placed by a surgeon, gastroenterologist, or other medical professional, using a flexible catheter with a grasping forceps in the catheter, placed through the working channel of a gastroscope or endoscope. For loading the staple, the grasping forceps grasps the central loop of the staple and pulls the staple in the catheter. The catheter is placed through the working channel of the endoscope. When in position the tip of the catheter is firmly applied against a device being implanted or against tissue for stapling, the grasping forceps is pushed out of the catheter, which expels the staple. The staple immediately resumes its original wing shape so that the wings open and the staple is placed in position.

In order to remove the staple, under endoscopic control, the tooth of the grasping forceps seizes the loop in the middle of the staple and the staple is pulled back into the catheter. Then the catheter with grasping forceps and staple can be removed out of the body of the patient.

Another aspect of the invention is a surgical method comprising attaching a medical device to the inner mucosa of a gastro-intestinal tract of a patient with a the gull shaped staple using a conventional straight viewing video or fiberoptic endoscope or a lateral viewing endoscope for positioning of the staples. In order to assure stability and avoid a back-jump of the flexible endoscope while firing, an inflatable balloon can be attached at the tip of the endoscope and inflated before firing the staple. The balloon is deflated after firing so that the forceps can move and release or ungrasp the staple. Alternatively, an overtube with an internal part sold by US Endoscopy under the name the Guardus overtube can also be used with or without the internal introducer part to give stiffness to the endoscope when firing the staple.

Another aspect of the invention is a surgical method comprising attaching medical devices to the inner mucosa of a gastro-intestinal tract of a patient with a the gull shaped staple using ultrasound real time visualization and a flexible endoscope in order to determine exact penetration of the wall of the GI tract.

An additional aspect of the invention is an article useful for implanting a medical device comprising an electrical lead, a flexible joining member, and a gull shaped staple at a terminal end used for attaching an electronic pace setter.

Another aspect is a method of implanting a medical device having an electrical lead comprising providing a terminal staple of the aforementioned gull shaped configuration on an electrical lead or a flexible joining member attached to an electrical lead, placing the staple in a first lumen of the lumen catheter, injecting saline solution through the second lumen, and using ultrasound to implant the staple, thereby fixing the electrical lead of the medical device in a predetermined layer of the GI tract.

Another aspect of the invention, a device as described in my U.S. Pat. No. 6,764,518, referred to as the GARD device, can be inserted through the mouth and the esophagus and, when located at the intersection of the esophagus and stomach mucosa, a ring portion of the GARD device is stapled to a hiatus hernia with the gull shaped staples using a flexible endoscope with forward view or lateral view as in a standard gastroscope or a lateral view duodenoscope, which facilitates precise placement and stapling. In some embodiments the ring described in my aforementioned U.S. Pat. No. 6,764,518, FIG. 1, is modified. Oval holes are punched through the ring at regular intervals around the circumference. In certain embodiments, the spring in the ring has 10 loops and, under every second loop, an oval hole is punched through the ring. The oval hole has to be wide enough to fit the tip of the flexible catheter holding the staple. Around the ring, a narrow 0.2 mm to 0.3 mm net or mesh of polypropylene or a net made of another biocompatible material dipped in silicone is glued around the ring to close the holes. This configuration allows the tip of the catheter with the staple to fit into the niche created by the holes to avoid slippage of the catheter before shooting the staple. Also, the thinner wall created by the net will allow the staple to hold the ring and attach the ring and the device to the wall of the esophagus/hernia. In order to make the oval holes more visible endosopically, a colored marking such as a black ring of biocompatible silicone around the hole can be added to make the niche more visible for the endoscopist and help him/her see the holes for stapling.

In certain embodiments, a balloon is attached outside of the endoscope. Before shooting the staple with the catheter, the balloon is inflated. The inflated balloon blocks the tip of the endoscope in the ring of the GARD device or the ring of the OB tubes and prevents the endoscope from jumping back or backfiring when the staple is fired. The inflation of the balloon allows better penetration of the staples through the ring and into the tissues without risking a back movement of the flexible endoscope and incomplete penetration of the staple, which can happen when no balloon is used. After the staple is fired, the balloon is deflated. The selection of the diameter of the inflated balloon depends on the diameter of the endoscope and the inner size of the ring. The diameter of the inflated balloon in some embodiments is between 5 mm and 25 mm, preferably between 10 mm and 20 mm. The purpose of the balloon is to make the tip of the flexible endoscope more rigid. Alternatively the inner tube of a Guardus overtube can be used. The inner tube acts like a rigidifying sheath for the flexible endoscope and allows better penetration of the staples through the silicone ring, closing the holes and the tissues to which the device has to be attached.

In the case of surgical treatment of obesity, the invention comprises a device as described in my PCT/US06/35568 filed Sep. 11, 2006, which is hereby incorporated by reference, describing a GARD and an alternative procedure to staple the stomach endoscopically and reversibly vertically or horizontally in order to do a gastric restrictive operation for moderate obesity or yet to staple a by-pass tube from the esophagus to the small bowel and pace the gastro-intestinal tract to allow progression of the alimentary bolus for morbid obesity.

In my PCT/US06/35568 in which tubes with an upper ring to treat obesity are described, said upper ring may also be modified with oval holes and netting wrapped around the ring to allow implantation of the reversible staples. The holes can be underlined in some embodiments with a different color biomaterial such as black silicone.

In some embodiments, the staple of the invention is constructed of a single length of nitinol wire formed into a central loop, two parallel-like arms with each of the arms extending from the parallel direction in two opposing courses formed of an arc extending upwardly and outwardly and two ends comprising sharpened endpoints, the endpoint being more than about 0.5 mm above the top part of the central loop, depending on the size of the staple, the arms bendable under resistance; the article adapted to fold so as to fit within a flexible tube having an internal diameter of about 2 mm to 4 mm and to unfold elastically when pushed out of the tube at a location through the medical device.

The staple is preferably constructed of nickel-titanium alloy, and staples of such material are novel and advantageous for several reasons. In most embodiments the staple will use the hyperelastic characteristic of nickel-titanium alloy, allowing folding under stress in a narrow tube for placement in a catheter and resuming the original position when unstressed without permanent deformation of the staple.

For applications where temporary staples are needed, the staples can be constructed of biodegradable material, as long as the material is elastic enough to return to normal position after bending the tags to a substantially parallel position during the insertion steps. Such temporary applications include stapling to the esophagus or gastro-intestinal tract of captors monitoring pressure, pH and/or temperature or any other physical parameter. The biodegradable staple can be made of absorbable materials such as lactide, glycolide, or e-caprolactone for such temporary placement.

For permanent applications such as with a GARD device, the flexible joining material can be made in implant grade steel, nitinol, surgical thread, or implant grade polymer such as nylon, for example. However, nitinol (nickel-titanium alloy) is the preferred material because of its hyperelastic characteristics. The wing at each end of the joining member can also be made of steel, nitinol, implant-grade polymers such as nylon or any other biocompatible implantable material. In a preferred embodiment, the wing and flexible joining segment are each made of a non-absorbable material, preferably the aforementioned nitinol alloy which exhibits the flexibility needed when released from the catherer. In most cases the staples are constructed in an hyperelastic nickel-titanium alloy that does not use the configuration changes from martensite to austenite. The hyperelastic characteristics of the nickel-titanium alloy allows the staples to be pulled (loaded) in a relatively narrow catheter of 2 mm to 3.0 mm in diameter and when released to conserve the hyperelastic characteristics and almost instantly resume the original wing shaped configuration to function as a staple. To remove the staple, in one embodiment a toothed forceps grasps the loop of the staple and the staple is pulled back into the catheter for removal through the endoscope. An important advantage of certain embodiment of the invention is the reversibility of the stapling operation and the simplicity of the removal of the staples.

For treatment of IBS, one or more manometric probes are placed in the colon using the stapling system of this invention. The manometric probes are described in PCT/US03/13773, which is hereby incorporated by reference. The staple can attach a device to the alimentary tract but can also be used directly on the mucosa, often in pairs linked by a central ring, either to create a pleat or to staple two opposite walls of the alimentary tract together as in stapling the posterior wall to the anterior wall to create a gastroplasty. Also, part of each staple is flat, not curved, so as to stay in the muscularis layer of the gastro-intestinal tract. The staple ends are sharpened but at introduction the hyperelastic nitinol staple can be introduced in a smaller needle and, when released in the tissues, adopts the original configuration. Also, when using an endoscope, the catheter can be placed in a niche of a ring to avoid slippage, then the staple can be expelled through the catheter with a hook or a small forceps.

Several shapes of symmetrical staple wings can be used in order to allow suitable stapling force, yet allow the staple to be removable.

The staples can be kept at room temperature as their hyperelastic characteristic is used in stapling reversibly at flexible endoscopy.

In order to attach two opposite staples together to create as gastric reservoir to treat obesity in a vertical or horizontal line of staples, two staples are first placed opposite to each other on the posterior and anterior walls of the stomach. Then a thread is passed with a forceps and the flexible endoscope through the mouth and through the central ring of the staple and pulled out again. A standard gastroscope or, preferably, a double channel endoscope, can be used to facilitate the passage of the thread through the central loop and pulling it through the loop and out again. The same procedure is repeated with the other staple. Two double threads are then at the mouth of the patient and a small thin-walled titanium tube is then slid over the four pieces of thread through the mouth and esophagus into the stomach, allowing approximation of the anterior and posterior walls. Once the small titanium tube is in placed near the two central rings of the two staples, the tube is crimped with a forceps passed in the second working channel of the endoscope. The four threads are cut and the same procedure is repeated to create a small reservoir. A horizontally placed line of staples can be placed with a small opening for food. This operation mimics the laparoscopic banding operation, with the advantage of being done non-invasively through the mouth with staples that are reversible.

Alternatively, a small circular joining element can attach both central loops of the two staples to gether.

In some embodiments a tilt-tag is attached to the central loop with a non-resorbable surgical thread to prevent the staple from being placed too deeply and to help in retrieving the staple.

When a tilt-tag is used, a catheter having an outer sheath and a forceps with a tooth can be used to grab the central loop and pull the staple into the catheter to load the catheter and place the tilt-tag in the outer sheath. In some embodiments the catheter can have a long flexible part and a short metal tube, for example about 3 to 4 cm, which will lodge the staple. The end of the catheter can be cut in order to end as a short 3 mm needle with a thin slit in the upper part of the tube to let the surgical thread linking the staple in the flexible catheter and the tilt-tag placed in the outer tube. The staple with tilt-tag is loaded by pulling the central loop of the staple into the catheter with the toothed forceps, for example. The surgical joining thread passes through the narrow slit of the needle and the tilt-tag is placed in the outer sheath. In these embodiments, a larger diameter catheter may be needed in order to accommodate the tilt-tag in the outer sheath. In some embodiments an endoscope or gastroscope with a 3.7 mm or larger channel such as the Olympus GIF 1T 30, a GIF XT30, a FIG. 2T 20, or video endoscope XTQ 160 can be used. Certain endoscopes have multiple channels, which are suitable for use with staples having tilt-tags.

BRIEF DESCRIPTION OF THE DRAWINGS

FIG. 1b illustrates a side elevational view of the staple of FIG. 1a.

FIG. 18 is a partial cross-sectional view of a stomach which illustrates a horizontal line of staples creating a small reversible reservoir to treat obesity.

FIG. 19 is a view of two double threads placed through the loops of the staples and a cross-sectional view of a thin-walled tube sliding on the threads in order to join two stomach walls and create a gastric reservoir.

FIG. 20 illustrates the tube of FIG. 19 that has been crimped and blocking the threads to create the gastric reservoir.

FIG. 21 illustrates how two pairs of double threads passed in the central loop held together by the crimped tube separate the top part of the gastric reservoir from the main portion of the stomach in the bottom.

FIG. 23f illustrates a long OB tube reaching the jejunum and with a pace-maker and leads.

FIG. 24 illustrates a removable staple holding a manometric probe in the lumen for treatment of Irritable Bowel Syndrome (IBS).

FIG. 25 is a perspective view of an embodiment of a staple and tilt tag joined by surgical thread.

DETAILED DESCRIPTION

Figure 1A:
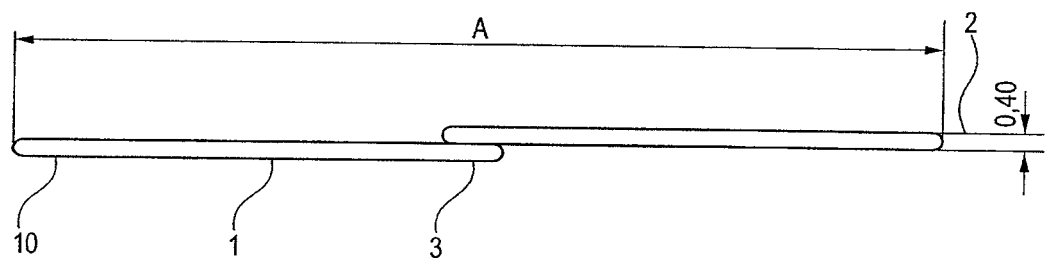
FIG. 1a illustrates a top view of an embodiment of a staple according to the invention.
Figure 1B:
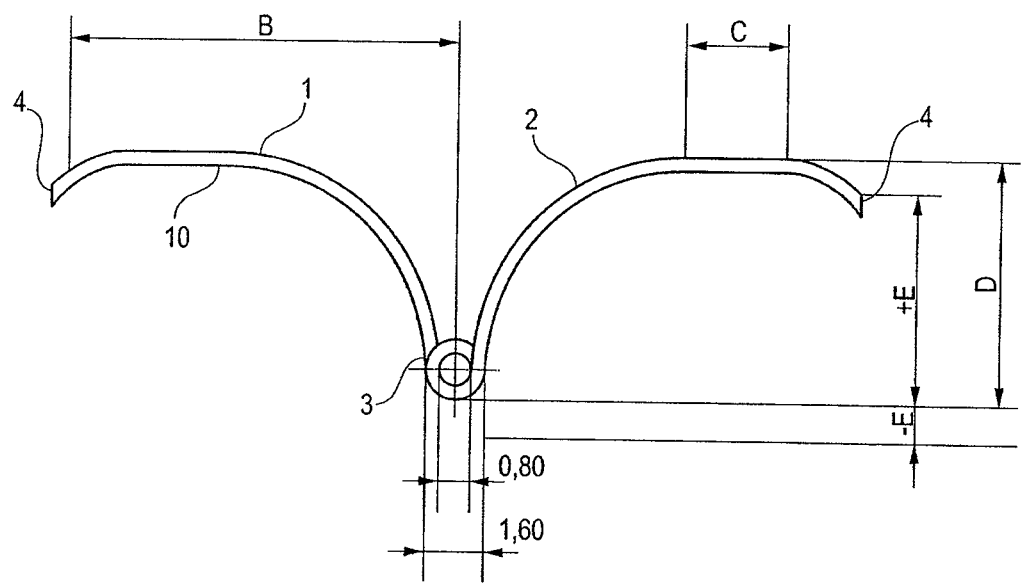
Figure 1C:
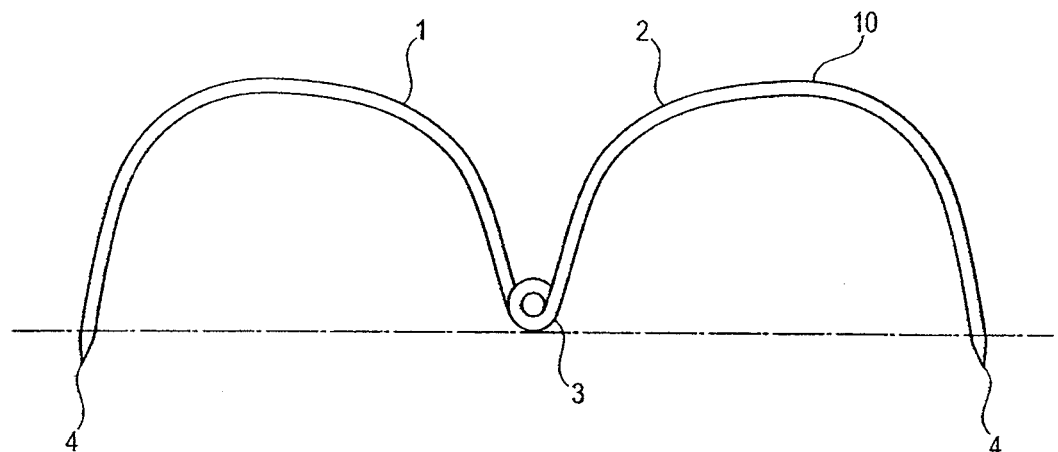
FIG. 1c illustrates a side elevational view of a second embodiment of a staple of the invention.

Referring first to FIGS. 1a and 1b, an example of a staple 10 of the invention is shown wherein a first 1 and a second 2 wing are joined perpendicularly at respective ends of joining member 3. In the illustrated embodiment, the staple 10 is molded in one piece from Nitinol, commercially available nickel-titanium alloy. Distance A in FIG. 1a varies between 4 mm and 30 mm but preferably 6 mm to 20 mm, and more preferably 10 mm to 16 mm. Preferably, the distance from the bottom of the loop to the endpoints is about 2.0 mm or more to avoid the endpoints piercing back into the lumen. Distance B can vary between 1 mm and 5 mm depending on the organ in which the staple is used (the stomach is much thicker than the esophagus or small and large bowel) but preferably is about 3 mm. Distance D in FIG. 1b can vary between 2 mm and 10 mm depending on the organ in which the staple is used (the stomach is much thicker than the esophagus or small and large bowel). Distance C in FIG. 1b can vary between 0.5 mm to 4 mm, more preferably about 2.0 mm. Importantly, Distance E which determines the distance between the base of the central loop 3 and the sharpened tip of wing 4 can vary between −2 mm and 10 mm (depending on Distance D), having a negative value when the tip 4 is below the base of the central loop 3 (FIG. 1c).

Figure 2:
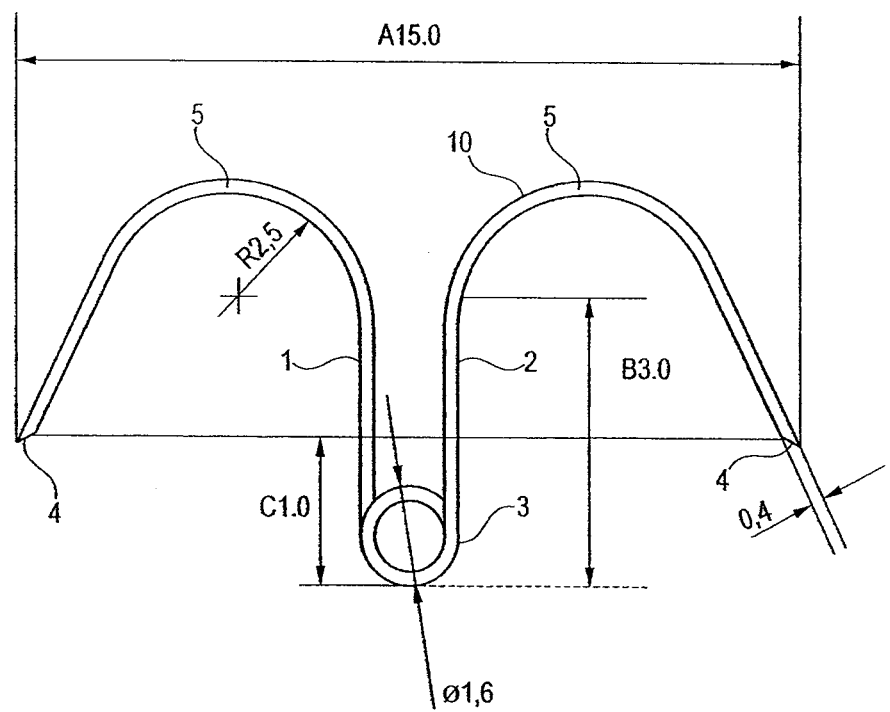
FIGS. 2, 3, 4, and 5 illustrate several additional embodiments of the staple according to the invention.

Referring to FIG. 2, an example of a staple 10 of the invention is shown wherein a first wing 1 and a second wing 2 are parallel at a portion adjacent to central loop joining member 3. Each of the wings 1 and 2 extend from the parallel direction in two opposing courses forming an arc 5 extending upwardly and outwardly and two ends 4 comprising sharpened endpoints, the endpoint being in this example a Distance D, of 1.0 mm above the top part of the central loop, but can be varied, depending on the size of the staple. Distance A, the width of the staple, is 15 mm in this example, and distance F, the length of the parallel segment between the bottom of the loop 3 and the beginning of the arc 5, is 3.0 mm in this embodiment.

Staple 10 is preferably molded in one piece from nickel-titanium alloy such as Nitinol, a brand of commercially available nickel-titanium alloy.

Figure 3:
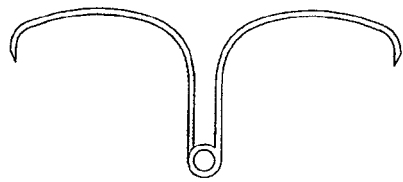
Figure 4:
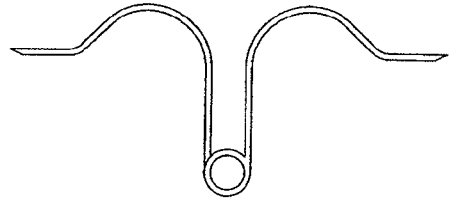
Figure 5:
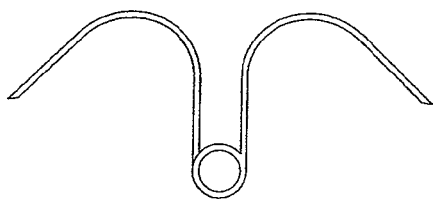

Referring now to FIGS. 3, 4 and 5, several variations of the staples are illustrated. In FIG. 3 both wings 1, 2 of the staples 10 are roughly perpendicular to the parallel elements 1a and 2a. In FIG. 4 the ends have an S shape and in FIG. 5 the ends are facing backwards towards the central loop.

Figure 6A:
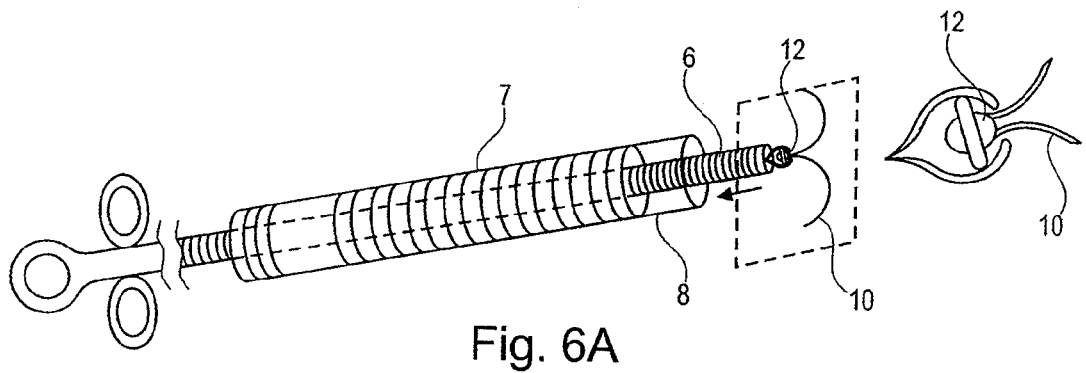
FIG. 6a illustrates an embodiment of a rounded tip grasping forceps holding a staple.
Figure 6B:
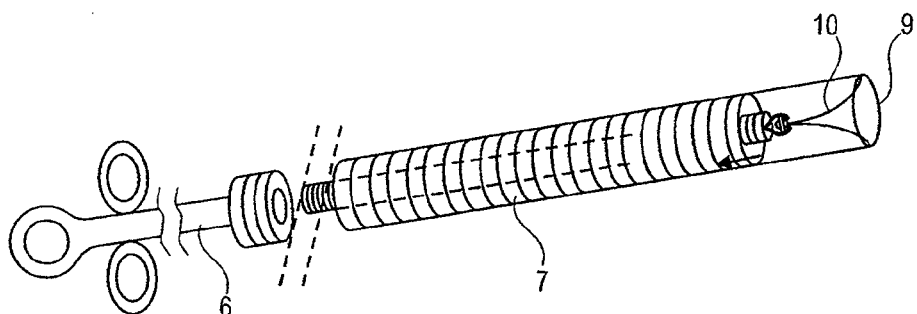
FIG. 6b illustrates an embodiment of a rounded tip grasping forceps holding a staple folded in a flexible tube

Referring now to FIGS. 6a and 6b, the staple 10 is pulled (FIG. 6a) with a grasping forceps 6 with a little tooth 12 and inserted in a flexible catheter 7 which is slightly wider than the diameter of the joining member, allowing both wings to bend inside the flexible catheter 7 as in FIG. 6b. The flexible catheter 7 acts as a sheath for the forceps 6 and staple 10 assembly. The flexible catheter 7 is preferably made in a Pebax thermoplastic elastomer flexible tube. A short tube 8 can be welded, glued or otherwise attached at the end of the Pebax flexible tube to avoid excessive friction of the endpoints 4 of the staples 10 when loading into the catheter 7 and particularly when expelling of the staple 10 in tissue is desired.

The flexible Pebax catheter 7 with the forceps 6 and the staple 10 are passed in the working channel of a standard endoscope. In order to place the staple 10 in tissue or through a medical device such as a GARD, the rounded tip 9 of the catheter 7 is placed against the device or tissue that has to be stapled (FIG. 10) and the staple 10 is pushed out with the forceps 6.

Figure 7A:
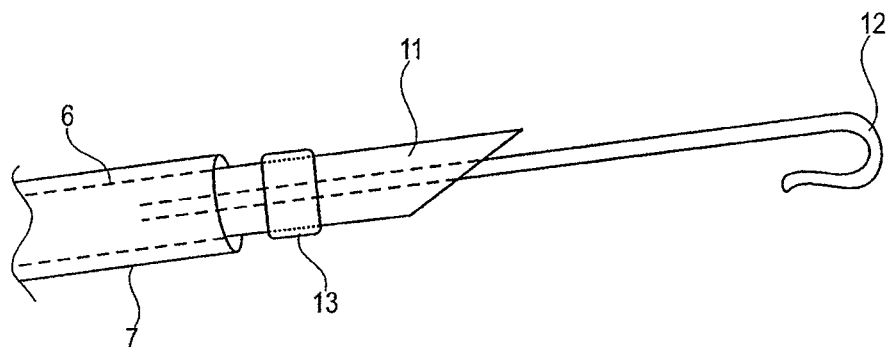
FIG. 7a illustrates an embodiment of a needle tipped flexible catheter with a stopper and a hook.
Figure 7B:
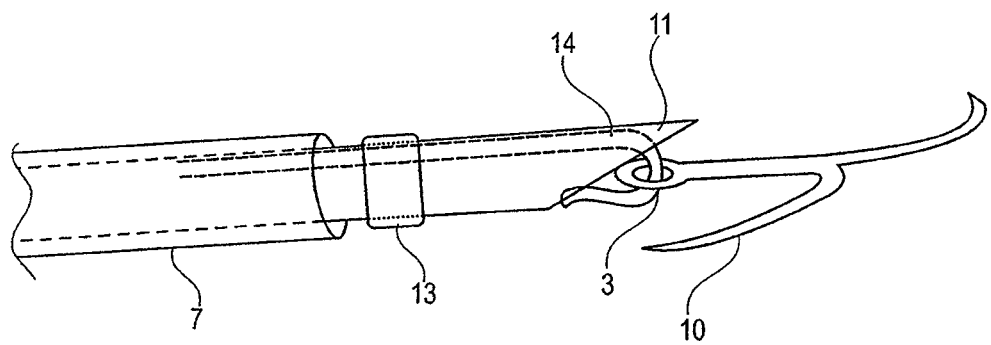
FIG. 7b illustrates an embodiment of a staple being grasped by a flexible catheter.
Figure 7C:
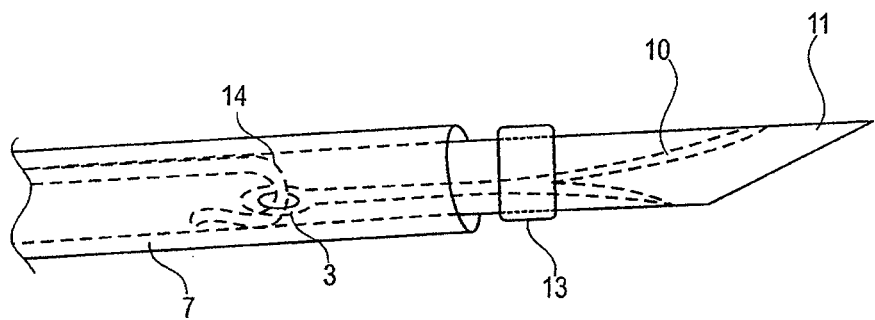
FIG. 7c illustrates an embodiment of a staple pulled into a catheter.

Referring to FIGS. 7a and 7b, a variation of the catheter is presented where the rounded end as in FIG. 6a is alternatively a sharpened needle 11. Rather than a tooth 12, a small hook 14 is used to grab the staple 10 by its central loop 3. In order to control the depth of penetration and to avoid causing lesions of organs beyond the wall of the esophagus or hernia such as the aorta or vena cava, a stopper 13 can be placed at a predetermined distance from the tip of the needle 11, for example between about 3 mm and 20 mm, and preferably about 4 mm to 6 mm. Such stopper can be used to hit the inner wall of the GARD and avoid deep penetration. Alternatively, a mark (not shown) on the needle 11 can inform the surgeon of the depth of penetration but will not control it. An echoendoscope EUS (not shown) could also be used for that purpose, however few endoscopists use EUS echoendoscope on a regular basis. A stopper or echoendoscope are not necessary when a round end catheter 9 (FIG. 6a) is used and the staple 10 with sharp endpoints 4 is used to staple the device and penetrate tissue, which is an advantage of the embodiment of FIGS. 6a and 6b.

Figure 8A:
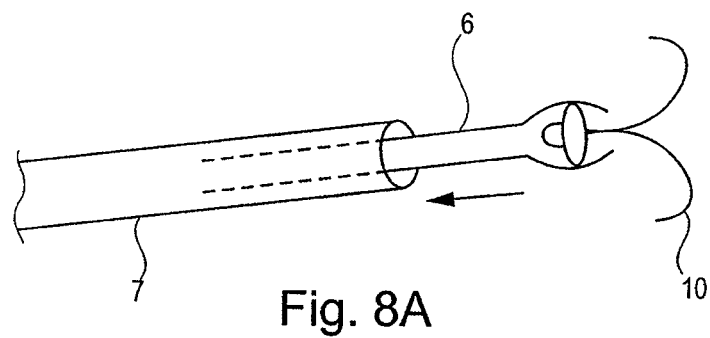
FIG. 8a to 8c illustrate the different stages of one of the embodiments of the staple when it is loaded then fired.
Figure 8B:
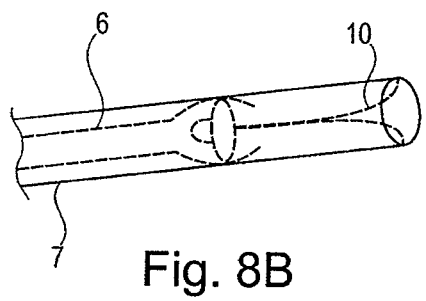

Referring now to FIG. 8a, a staple 10 is shown being grabbed by central loop 3 and being pulled in the direction of the arrow into the round ended flexible catheter 7 with the forceps 6. In FIG. 8b, the catheter 7 is shown loaded with the staple 10 being held by forceps 6.

Figure 8C:
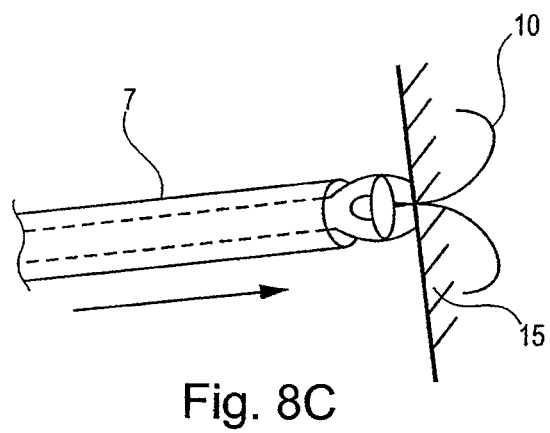

FIG. 8c illustrates firing out the staple of the round end of catheter 7 in tissue 15.

Figure 9A:
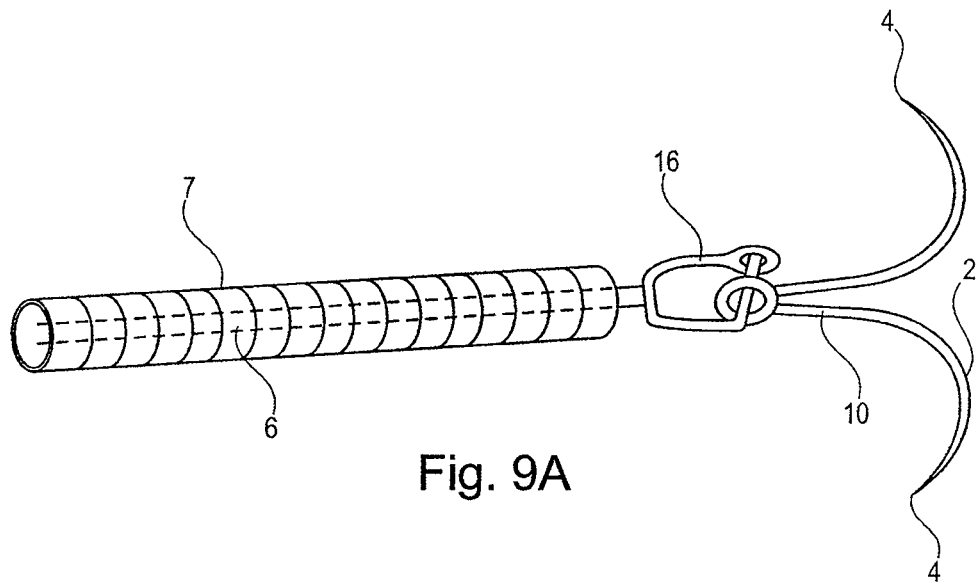
FIG. 9a illustrates a perspective view of a needle with a hook in a catheter grasping one staple according to the invention.

Referring now to FIG. 9a, a different embodiment of forceps 6 has a hook 16 that pulls the staple 10 in the flexible catheter 7.

Figure 9B:
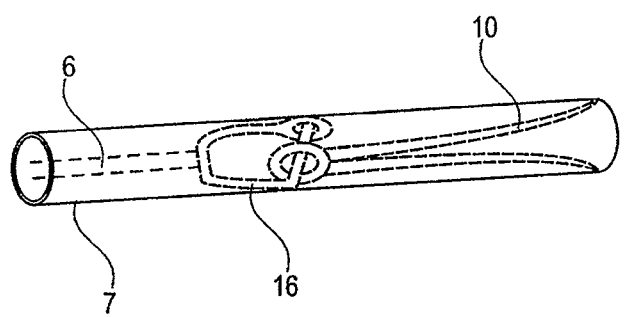
FIG. 9b illustrates a perspective view of a needle with a two-pronged rounded tweezer in a catheter loaded with one staple according to the invention.

FIG. 9b illustrates a staple 10 having been loaded in a catheter 7 with forceps 6 having hook 16.

Figure 10:
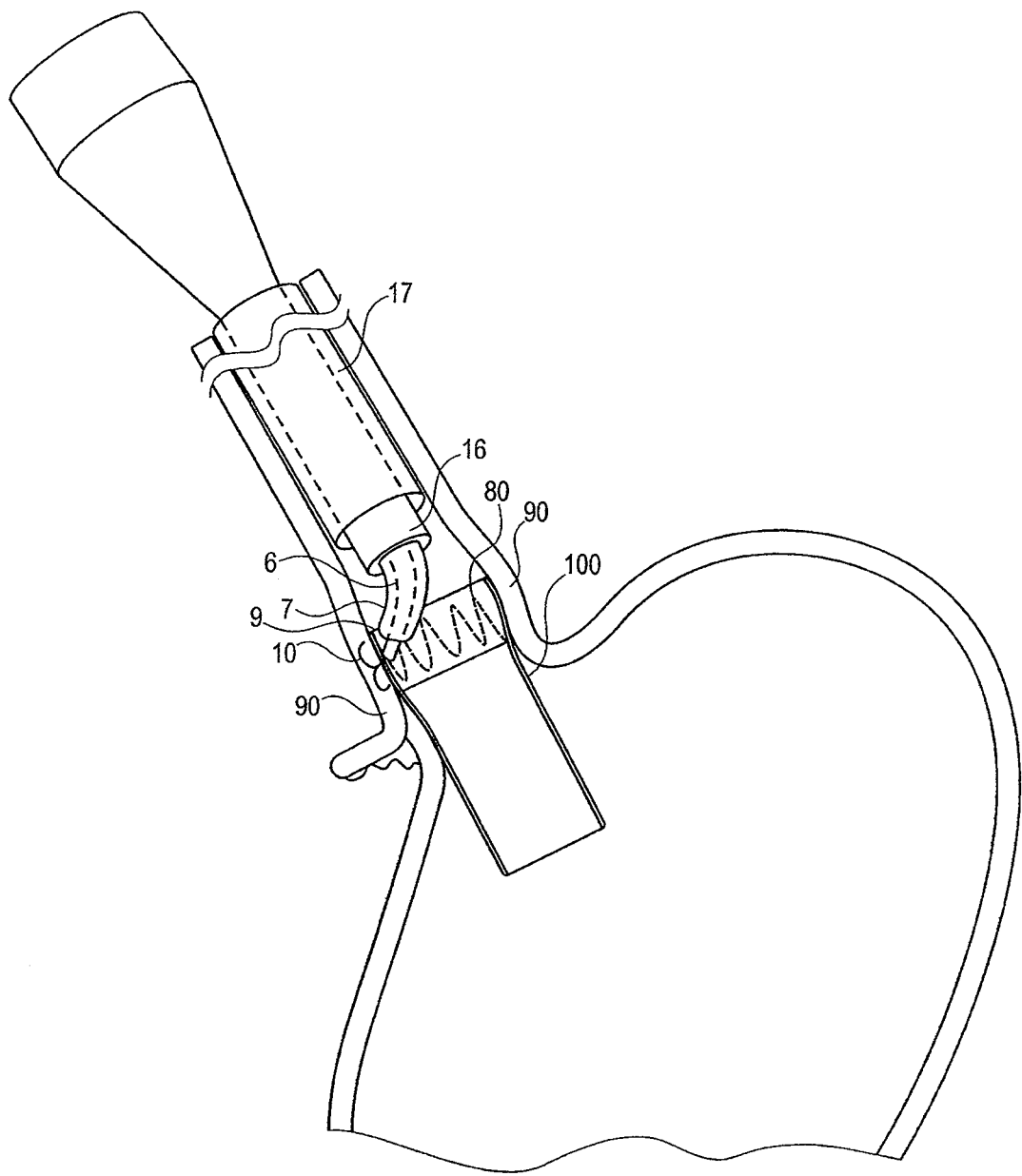
FIG. 10 illustrates a partial cutaway view of an esophagus with a straight viewing endoscope and a rounded end catheter inserting one staple of the invention through both a gastrointestinal anti-reflux device (GARD) and the inner mucosa.

Referring now to FIG. 10 GARD 100 anti-GERD valve is shown in place and the flexible catheter 7 with round end 9 have been passed through the flexible endoscope 16 through an overtube 17. The round tip 9 of the catheter 7 has been placed in a niche of the ring 80 and the staple 10 is positioned in the wall of the hernia 90. Several staples 10 will be placed around the perimeter of the ring 80. In this embodiment the central loop 3 acts to prevent staple 10 from going all the way through ring 80.

In this way, without tying complicated knots or using any pledgets or other devices to attach the free piece of thread, a reversible staple can be placed through the inner wall of the gastrointestinal tract and hold any device in place that needs to be held either for a long period of time such as the GARD that is placed for years, or shorter periods of time such as pressure, pH monitoring devices or other pressure devices that can be placed for a few weeks. When used with absorbable staples the monitoring devices will fall in the lumen of the esophagus, stomach or bowel once he staples and joining segment dissolve and will be expelled naturally. When used with the reversible staples, each staple 10 can be recovered by flexible endoscopy by pulling on the central loop 3.

Figure 11:
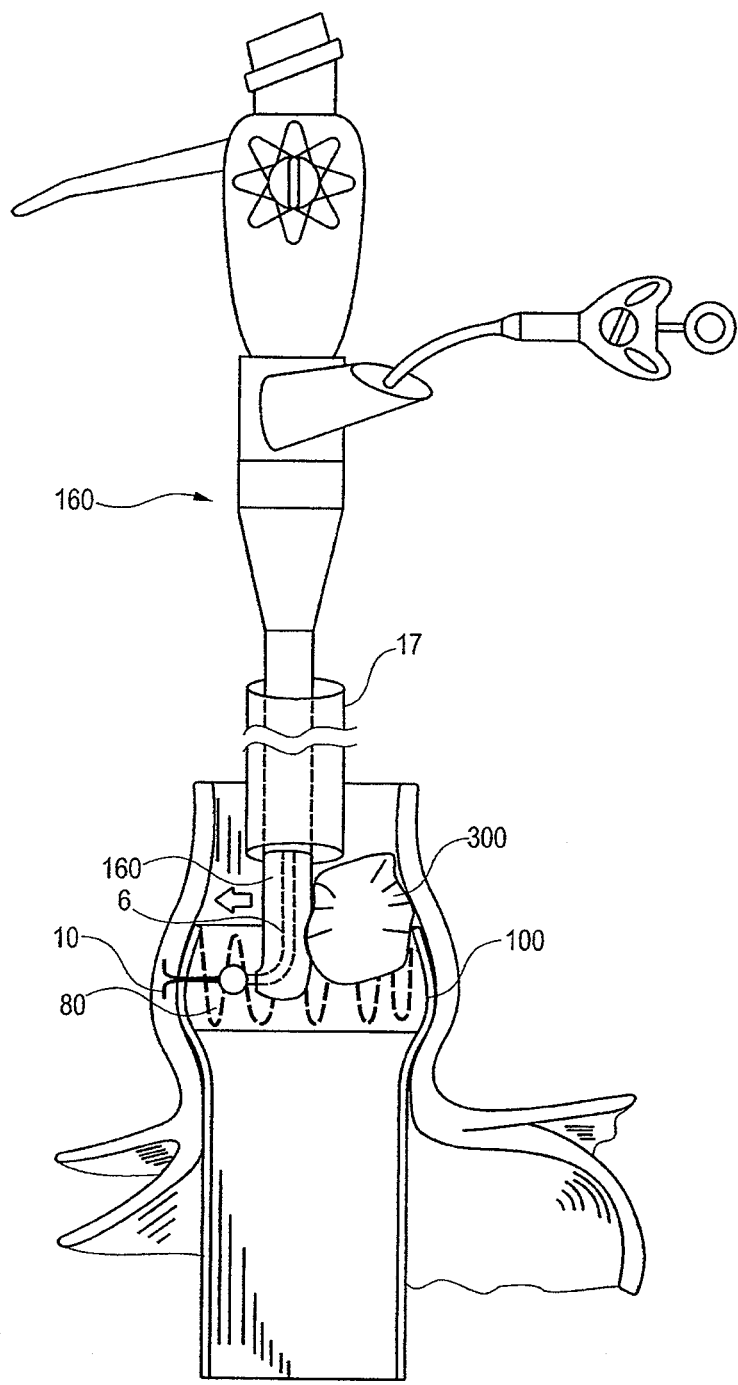
FIG. 11 illustrates a partial cutaway view of the esophagus with a lateral viewing endoscope, a needle catheter, and a balloon inserting one staple of the invention through both a GARD and the inner mucosa.

Referring to FIG. 11 a lateral viewing endoscope 160 (or a standard straight viewing endoscope) is placed through an overtube 17, and balloon 300 is blown to offer a certain amount of counter-pressure. The staple 10 is placed in the ring 80 of the GARD 100 for reversible stapling using the balloon 300 to maintain the forceps 6 toward the ring 80.

Figures 12A, 12B:
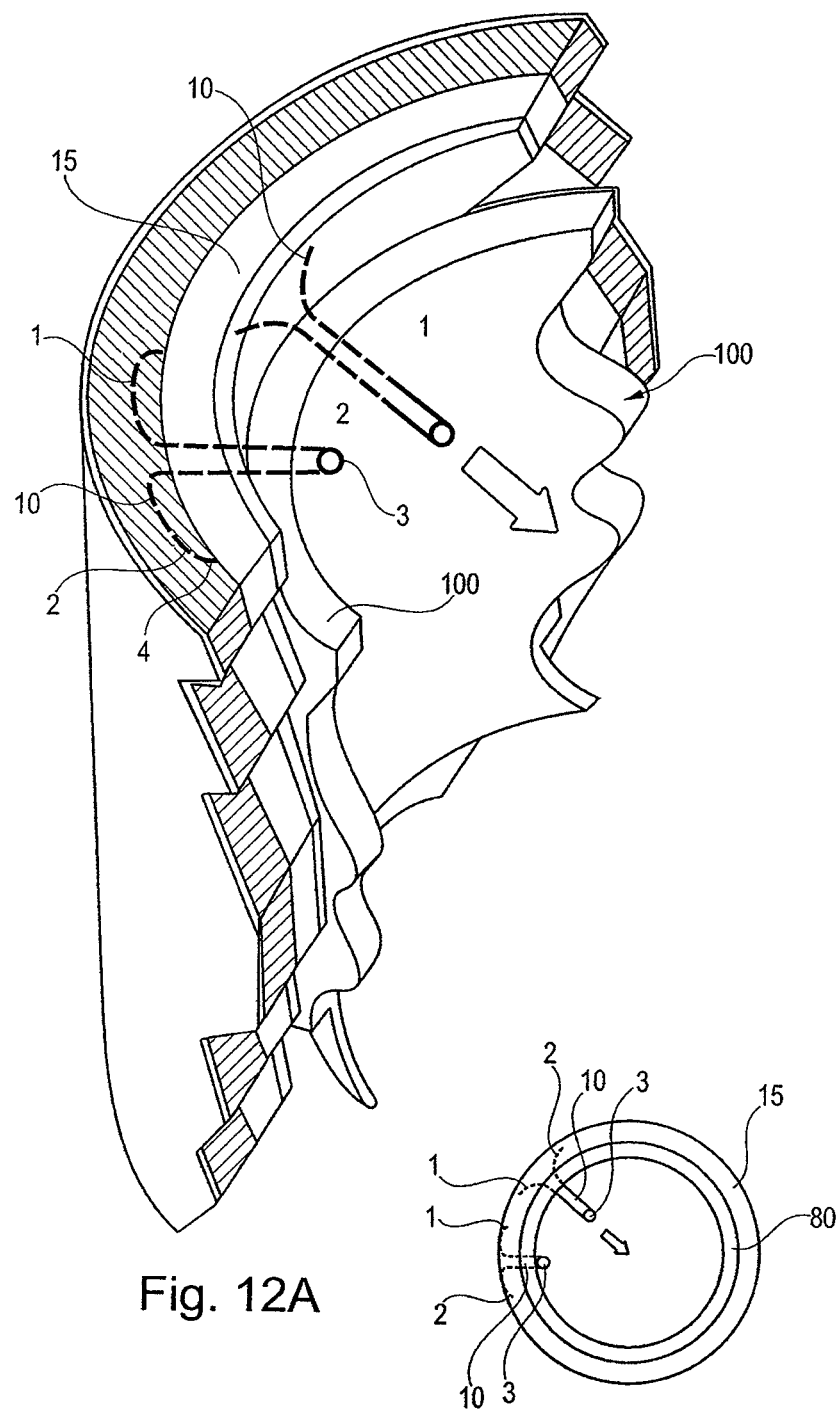
FIGS. 12a and 12b illustrate a side elevational cutaway view and a top cross-sectional view of a GARD stapled to the inner mucosa in the muscularis layer of the mucosa, with the staple being pulled out toward the inside in an uninstalling operation.

Referring to FIG. 12a an enlargement shows staple 10 in the muscular layer of the gastro-intestinal wall 15. Removal of the staple illustrated in FIG. 12b which shows a direction arrow toward the inside of esophagus 15 with staple 10 being pulled by central loop 3.

Figure 13:
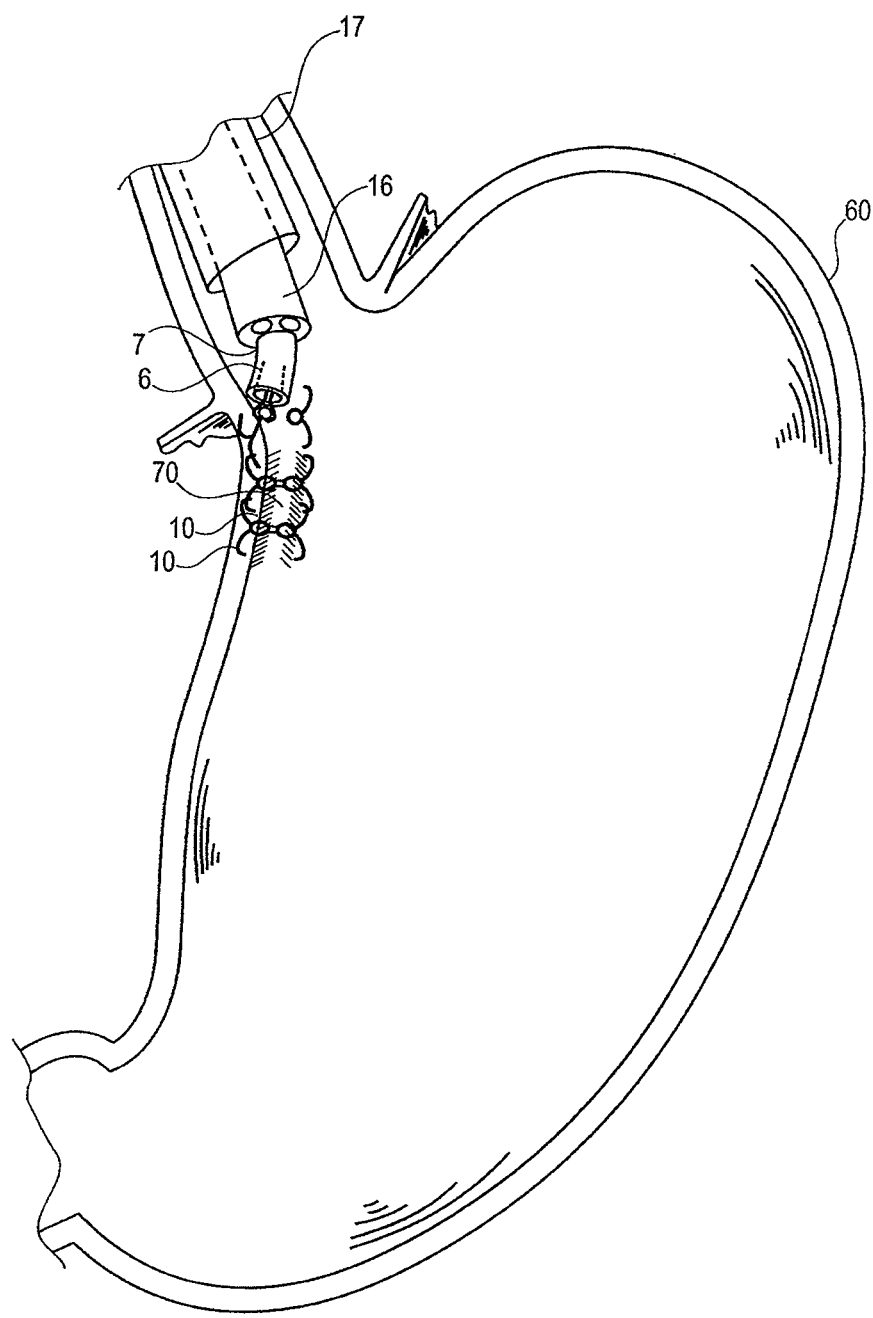
FIG. 13 illustrates the positioning of staples in pairs through a straight viewing gastroscope in order to create pleats to treat mild to moderate gastrointestinal reflux disease (GERD). A larger balloon (not shown) can be used to apply the end of the endoscope to the mucosa.

Referring to FIG. 13, staples 10 are placed in pairs at the cardia region of the stomach 60, creating a pleat 70 to block mild reflux. The endoscope 160, overtube 17, and needle 7 catheter with forceps 6 are also shown. The overtube or the inner part of the Guardus overtube sold by US Endoscopy can act as a counterpressure device where the balloon cannot be used because the stomach organ is large.

Figure 14:
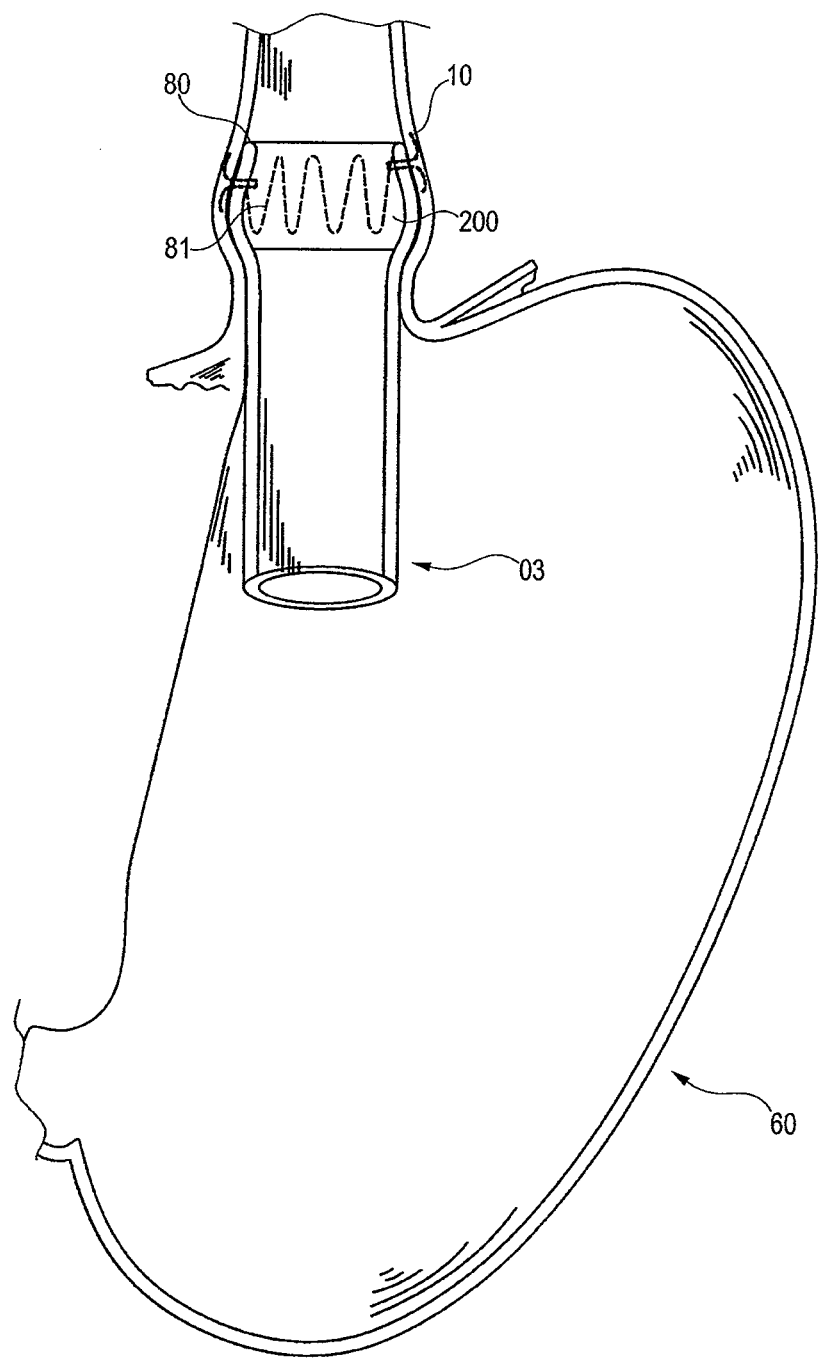
FIG. 14 illustrates the OB device stapled to the lower part of the esophagus or in a hiatus hernia.

Referring to FIG. 14 staples 10 attach an obesity OB 200 device using the same technique as described in placement of the GARD in FIG. 13. OB tubes 200 are preferably those disclosed in my U.S. Pat. No. 5,861,036 which is hereby incorporated by reference and are usually longer than 10 cm for treatment of obesity, using the ring disclosed in U.S. Patent Publication 20030009239 of Jan. 9, 2003, also incorporated by reference, preferably with the ring 80 having a zig-zag shaped nitinol spring 81.

Figures 15, 16, 17:
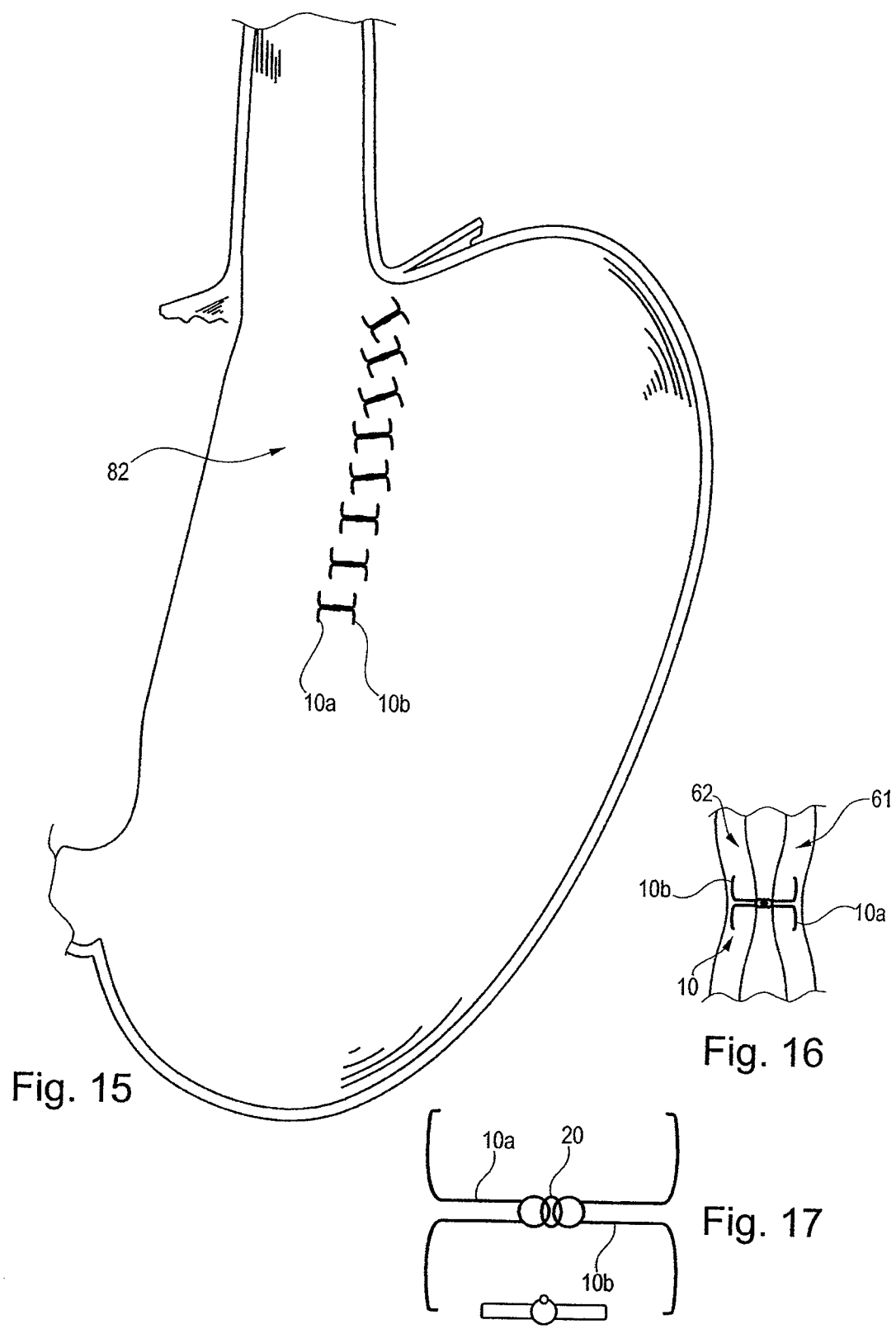
FIG. 15 illustrates a vertical series of pairs of staples stapling the anterior wall of the stomach to the posterior wall and creating a vertical banding gastroplasty for obesity, endoscopically and with reversible staples.
FIG. 16 is a cross-sectional view of posterior and anterior walls of a stomach stapled with two staples and joined with a ring.
FIG. 17 is a top view of two staples joined by a small open ring through the loops of the staples.

Referring to FIG. 15, a vertical reservoir 82 is made along the lesser curvature with a series of removable staples placed in pairs 10a and 10b and linked together to staple the posterior wall of the stomach 61 to the anterior wall 62 as shown in FIG. 16. This operation, made endoscopically with a straight viewing endoscope, allows a reversible reservoir to be made to treat obesity.

FIG. 17 shows detail of the linking of the two staples 10a and 10b of a pair. The staples 10a and 10b can be linked by a ring 20 or sutured together by two threads as illustrated in FIG. 18 which shows a horizontal endoscopic reversible stapling of the stomach for obesity. A small reservoir is made in "A". An anterior reversible staple 10a is placed on the anterior wall 62 with a double thread 30 to the mouth, a second reversible staple 10b is placed on the posterior wall 61 of the cardia of the stomach 30 with a thread 30 and a small tube 40 is slid from the mouth on both threads and crimped in place 50 as illustrated in FIG. 19, FIG. 20 and FIG. 21. Both threads are cut as in FIG. 21. This procedure is repeated along the width of the cardia leaving a small passage for food. This procedure creates a reservoir A similar to the reservoir currently created by the prior art laparoscopic band, but endoscopically and reversibly according to the invention.

The process of linking two staples can also be used to repair tears in a stomach or esophagus. Such tears can be accidental or can be intentional. A relatively new technique involves intentionally perforating the stomach in order to do operations endoscopically but outside of the stomach. A problem faced in the use of this new technique is how to close the perforations which were intentionally made. The use of two staples 10 and 10a (FIG. 17) with thread connecting them, one on either side of the tear, can be used to repair such tears.

Figure 22:
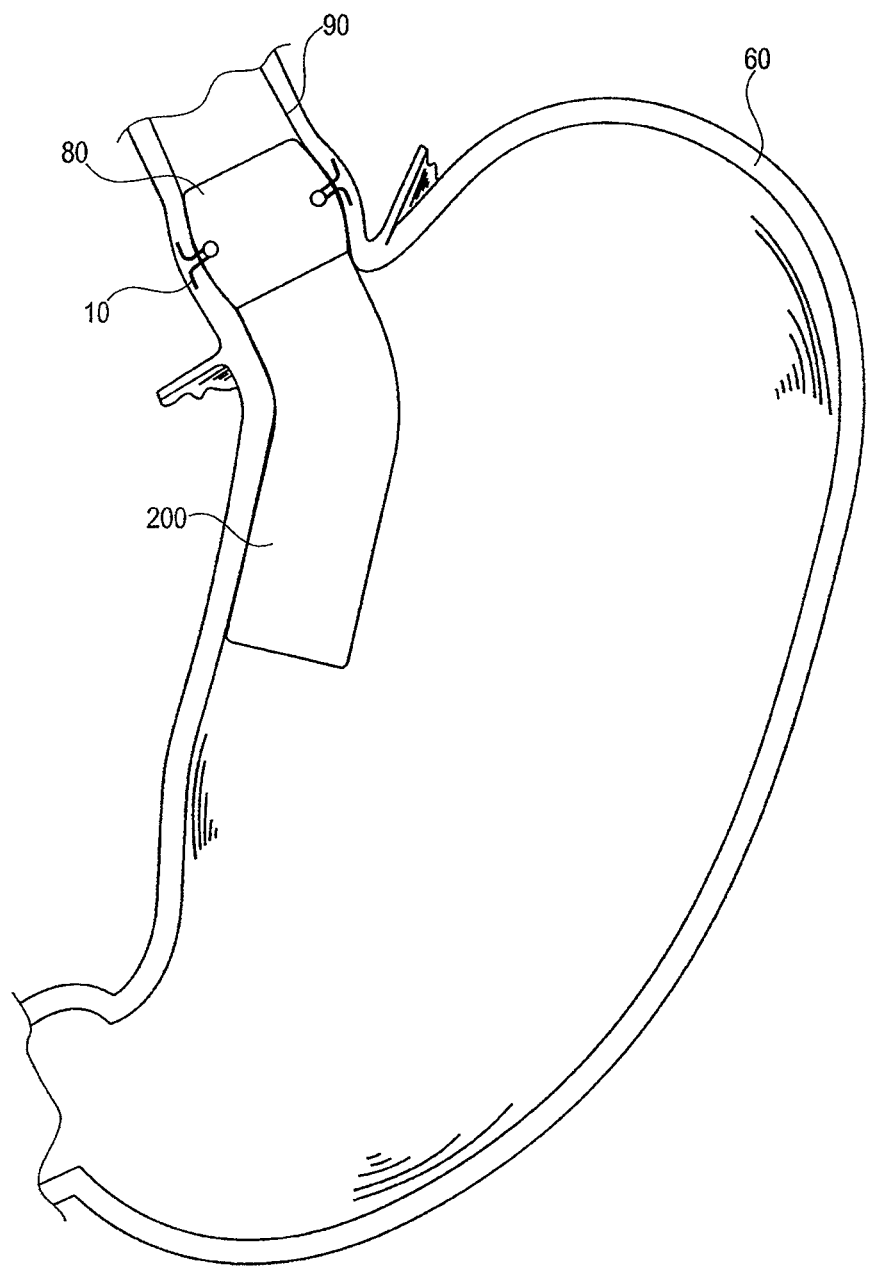
FIG. 22 is a cross-sectional view of a stomach and a perspective view of a GERD tube stapled from the lower esophagus along the lesser curvature of the stomach passing the middle of the stomach, creating a vertical reservoir similar to vertical banding gastroplasty.

Referring to FIG. 22, an obesity tube 200 is introduced in the stomach 60, stapled 10 to the hiatus hernia 90. This tube 200 creates a small reservoir as in FIG. 14 but is longer and easier to staple in place than creating a reservoir as in the operation described in FIG. 15 with a series of pairs of staples.

Figure 23A:
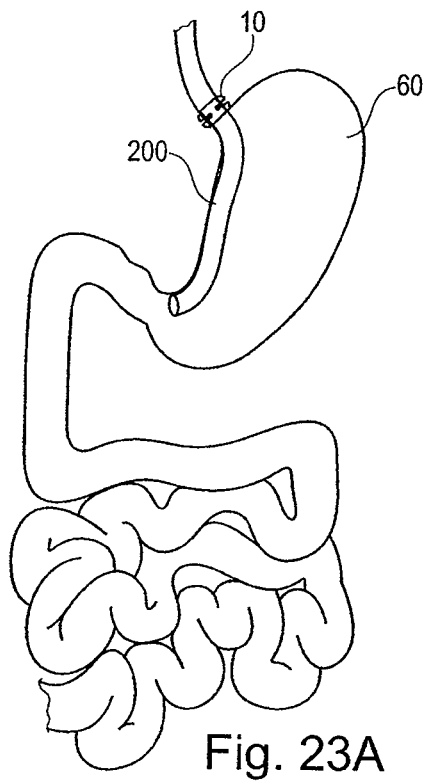
FIGS. 23a thru 23e illustrate different lengths of OB tubes creating internal by-pass tubes stapled from the lower part of the esophagus through the stomach (FIGS. 23a and 23b) duodenum (FIGS. 23c and 23d) or junction of duodenum and jejunum (FIG. 23e).

Referring to FIG. 23a, an internal by-pass tube 200 is introduced in the stomach and stapled 10 to the lower esophagus or hiatus hernia 90, allowing food to pass directly into the stomach 60.

Figure 23B:
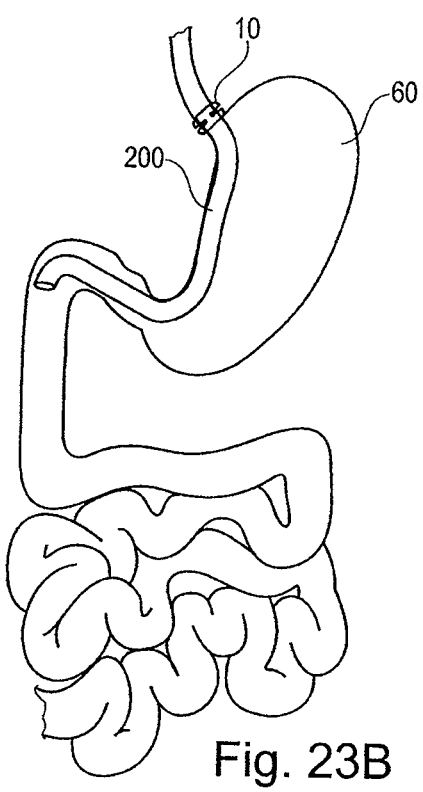

FIG. 23b illustrates total gastric bypasses according to the invention.

Figure 23C:
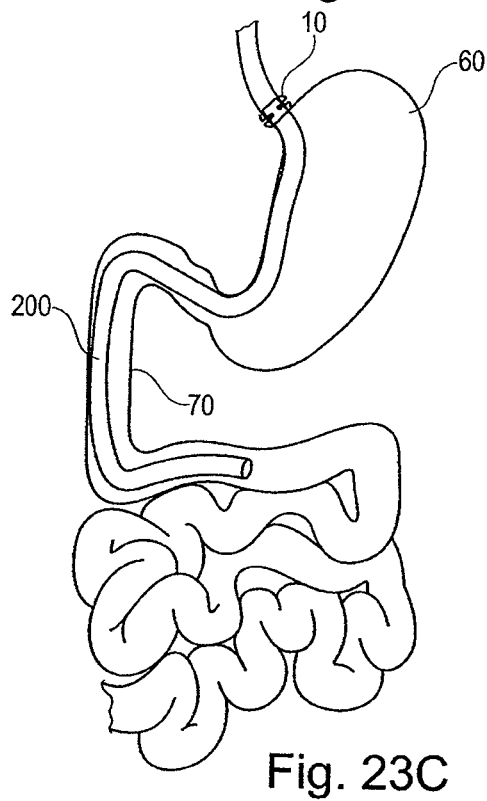

FIG. 23c illustrates total gastric bypass and partial duodenum 83 bypass with bypass tube 200 and stapled 10 to lower esophagus 84.

Figure 23D:
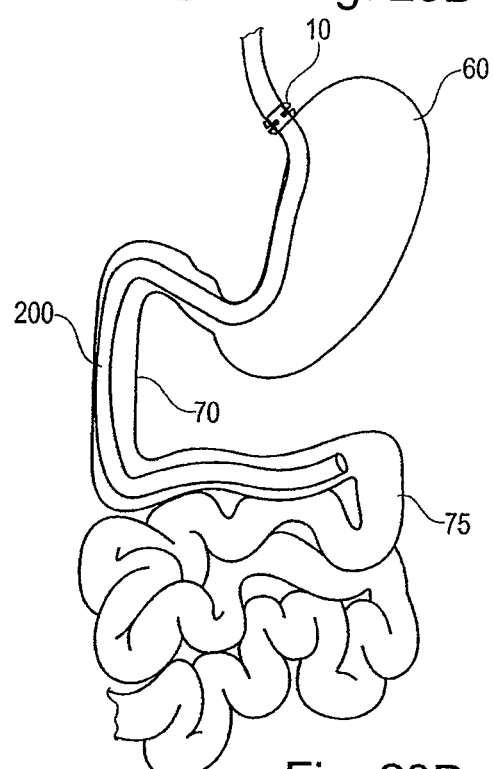

FIG. 23d illustrates a total gastric 60 bypass and total duodenum 70 bypass tube 200. The tube 200 can be semipermeable to allow fluids to pass but stops food particles to enter the stomach 60, duodenum 83, and proximal jejunum 75, causing a calibrated malabsorption. The length of the tube 200 is calibrated according to the excess weight loss, creating a "pseudo" short bowel syndrome.

Figure 23E:
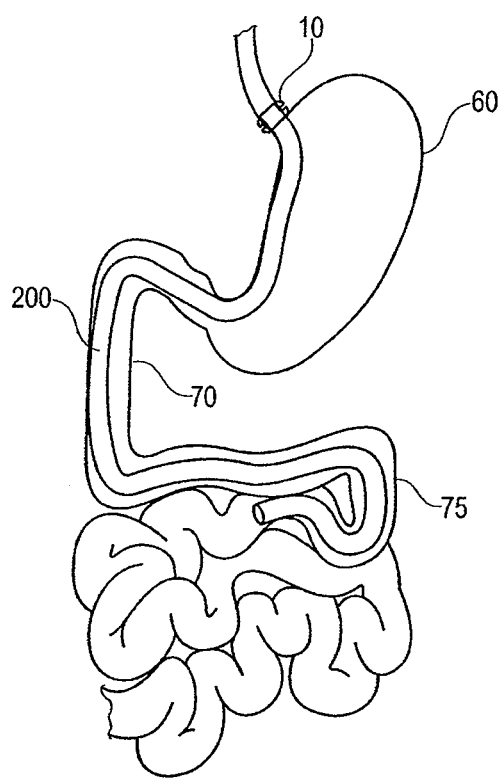

FIG. 23e illustrates a total gastric 60 bypass with total duodenum 83 bypass and partial intestinal (jejunal 75) bypass.

FIG. 23f illustrates a total gastric 60 bypass, total duodenum 83 bypass, partial intestinal (jejunal 75) bypass with a stimulator in the form of a gastrointestinal pacemaker 500 and the leads 600. The tube can let gastric and duodenal water secretions penetrate in the tube 200 but not to leave it, thereby decreasing the length of small bowel used for absorption of food and causing weight loss. The tube leaves space 65 between the wall of the duodenum 83 and the external wall so that bile secretion and pancreatic secretions as well as gastric secretions can flow freely. A stimulator 500 can be used to pace the stomach 60, duodenum 83 and small bowel to allow peristaltic contractions (not shown) transmitted to the inner tube for progression of the bolus of food in the tube. Contractions induced to the gastrointestinal tract by the pace setter stimulator 500 increase the pressure in the bypass tube 200.

Referring to FIG. 24 a staple 10 is placed in the wall of the colon 400 using the same technique as described in FIG. 10 using a colonoscope or sigmoidoscope. The staple 10 holds a manometric probe 450 that transmits pressure readings telemetrically to a sensor 480 held outside the body to treat irritable bowel syndrome (IBS).

Referring to FIG. 25, an embodiment of staple 10 having a tilt tag 18 attached with surgical thread 30 to central ring 3 and secured at tilt tag hook 50 is illustrated. Using the tilt tag 18 helps prevent implantation of the staple 10 too deeply in either GARD ring 80 (FIG. 30) or tissue 60 (FIG. 13).

Figure 26:
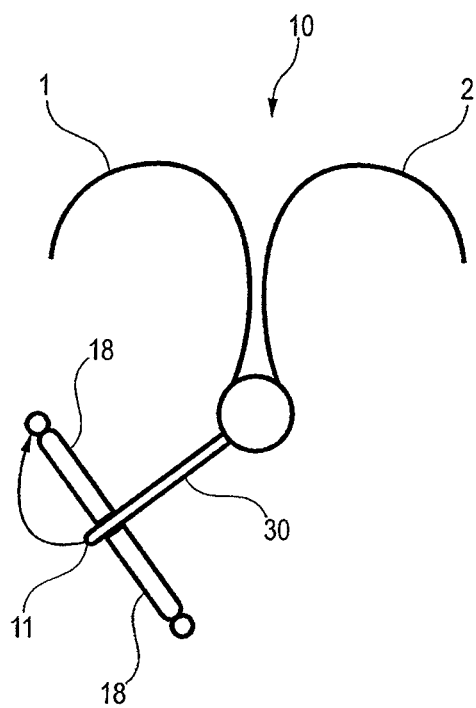
FIG. 26 is a perspective view of a staple joined by surgical thread to a second embodiment of a tilt tag via a knot of thread.

FIG. 26 illustrates an embodiment of tilt tag 18 using a knot 11 of thread 30 rather than the hook 50 of FIG. 25.

Figure 27:
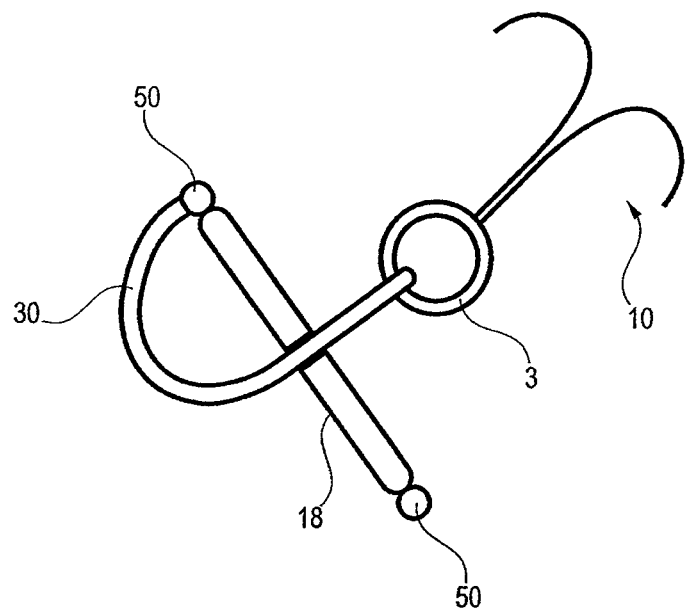
FIG. 27 is a perspective view of a staple joined to a tilt tag via a hook or ring at the distal end of the tilt tag.

FIG. 27 illustrates thread 30 engaged to hook 50 of tilt tag 18.

Figure 28:
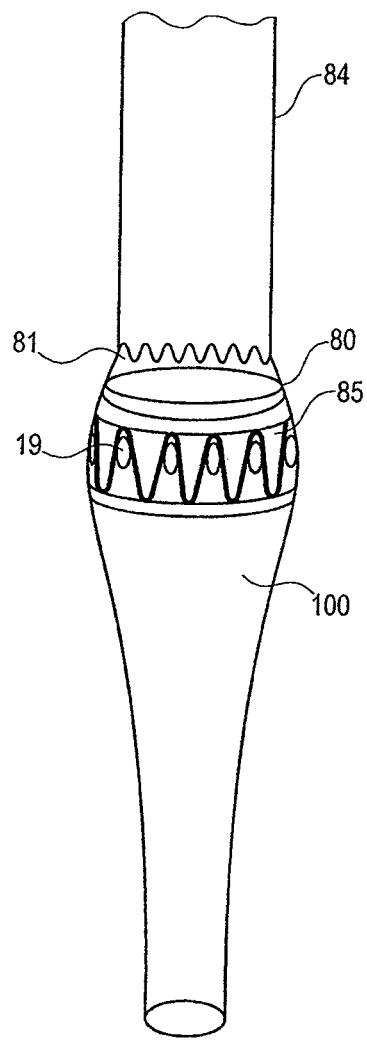
FIG. 28 is a GARD tube with placed in an esophagus, the tube having holes for placement of staples.

FIG. 28 illustrates a GARD valve 100 having thick ring 80 with holes 19 placed in esophagus 84. The ring 80 has a thin net 85, with silicone covering holes 19.

Figure 29:
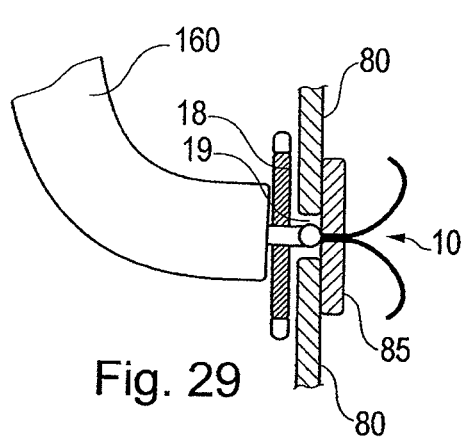
FIG. 29 is a view of a staple with tilt tag being inserted through a hole in a GARD ring with a flexible tube having a stopper.

FIG. 29 illustrates an example of a staple 10 with tilt tag 18 being inserted through a hole 19 in a GARD ring 80 with a flexible tube 7 having a stopper 13.

Figure 30:
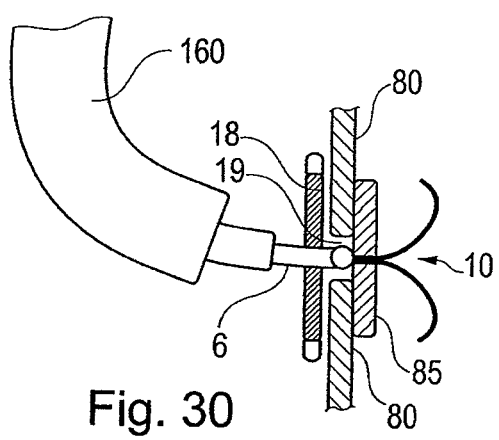
FIG. 30 is a view of a staple being inserted through a hole in a GARD ring with a flexible tube, forceps, outer sheath, tag, and thin net system.

FIG. 30 is an embodiment of a staple 10 being inserted through a hole 19 in a GARD ring 80 with a flexible tube, forceps 6, outer sheath 17, tag 18, and thin net 85 system.

Figure 31:
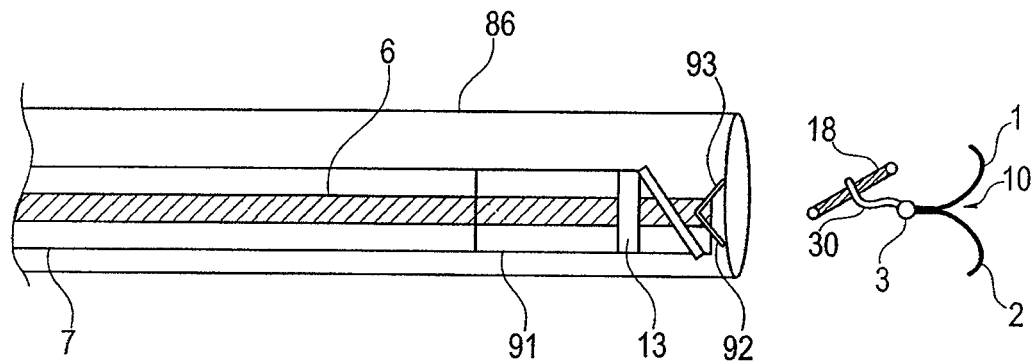
FIG. 31 is a side elevational partial cross-sectional view of a flexible catheter having a needle formed from a metal tube cut at a slant with edges sharpened, a forceps with a tooth in the central lumen of the needle, a stopper to limit the depth to which the needle may be inserted, a staple with tilt tag joined by surgical thread illustrated distal to the tip of the needle prior to being grabbed by the teeth or tooth of the forceps.

FIG. 31 shows a flexible catheter 7 having a needle 91 formed from a metal tube cut at a slant 92 with edges sharpened, a forceps 6 with a tooth 93 in the central lumen of the needle, a stopper 13 to limit the depth to which the needle 91 may be inserted, a staple 10 with tilt tag 18 joined by surgical thread 30 illustrated distal to the tip of the needle prior to being grabbed by the teeth or tooth 93 of the forceps 6.

Figure 32:
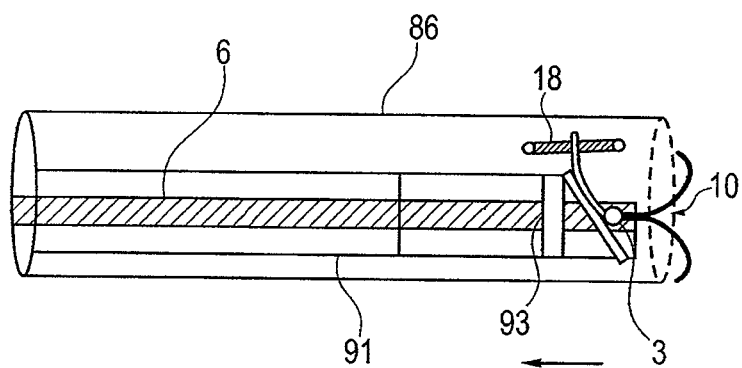
FIG. 32 is a side elevational view of the catheter-needle-forceps system illustrated in FIG. 31, illustrating the staple being pulled into the needle by action of the forceps grabbing the central loop of the staple and pulling in a proximal direction, with the tilt tag located in the lumen of the outer sheath but outside of the needle.

FIG. 32 is the catheter-needle-forceps system illustrated in FIG. 31, illustrating the staple 10 being pulled into the needle 91 by action of the forceps 6 tooth 93 grabbing the central loop 3 of the staple 10 and pulling in a proximal direction, with the tilt tag 18 located in the lumen of the outer sheath 86 but outside of the needle 91.

Figure 33:
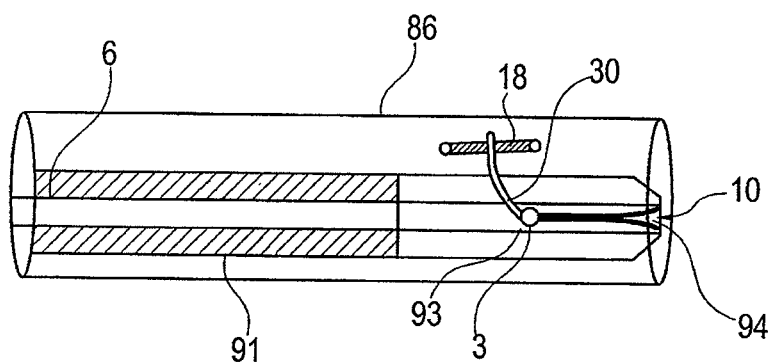
FIG. 33 is a top elevational view of the catheter-needle forceps system of FIG. 32, illustrating a lateral slit in the sharpened needle which receives the surgical thread connecting the tilt tag and staple when the staple is pulled into the needle and the tilt tag is placed in the lumen of the catheter outside of the needle.

FIG. 33 is a top view of the catheter-needle forceps system of FIG. 32, illustrating a lateral slit 94 in the sharpened needle 91 which receives the surgical thread 30 connecting the tilt tag 18 and staple 10 when the staple 10 is pulled into the needle 91 and the tilt tag 18 is placed in the lumen of the catheter 86 outside of the needle 91.

Figure 34:
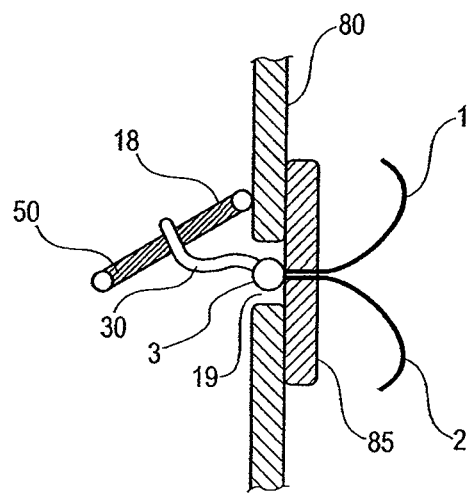
FIG. 34 is a side elevational cross-section of a staple-loop-thread-tilt tag system with the staple inserted through a hole in the GARD ring and through the net of the GARD, with the central loop of the staple within the ring and through the net of the GARD, with the central loop of the staple within the hole and the tilt tag loosely connected with thread to the central loop and disposed on the inside of an esophagus.

FIG. 34 illustrates a staple-loop-thread-tilt tag system with the staple wings 1, 2 inserted through a hole 19 in the GARD ring 80 and through the net 85 of the GARD, with the central loop 3 of the staple within the hole 19 and through the net 85 of the GARD, and the tilt tag 18 loosely connected with thread 30 to the central loop 3 and disposed on the inside of an esophagus. The thread 30 passed in the ring or hook 50 of at the ends of the tilt-tag 18 tightens the tilt-tag 18 against the loop 3 of the staple.

Figure 35:
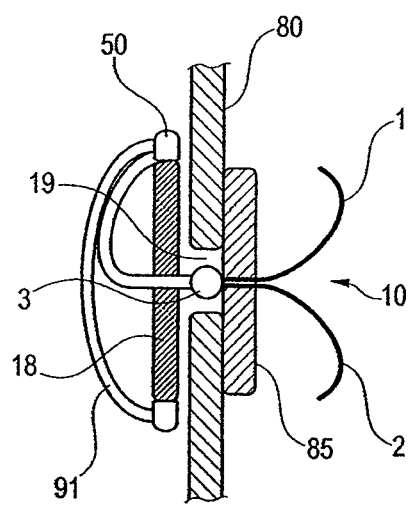
FIG. 35 is a similar view to FIG. 34, illustrating the thread passed in the ring or hook at the ends of the tilt tag and the tilt tag tightened against the central loop of the staple.

FIG. 35 is a similar view to FIG. 34, illustrating the thread 30 passed in the ring or hook 50 at the ends of the tilt tag 18 and the tilt tag 18 tightened against the central loop 3 of the staple.

Figure 36:
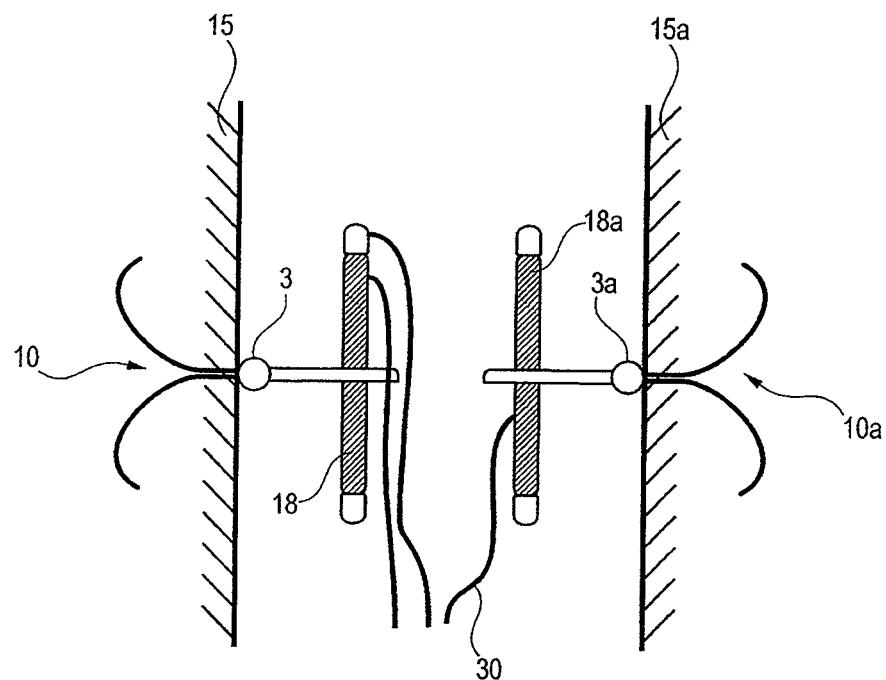
FIG. 36 illustrates a pair of staples inserted in two tissue walls of a stomach with tilt tags facing each other and thread from the first staple-tag system being used to join the second staple-tag system of the pair.

FIG. 36 illustrates a pair of staples 10, 10a inserted in two tissue walls 15, 15a of a stomach with tilt tags 18, 18a facing each other and thread 30 from the first staple-tag system being used to join the second staple-tag system of the pair.

Figure 37:
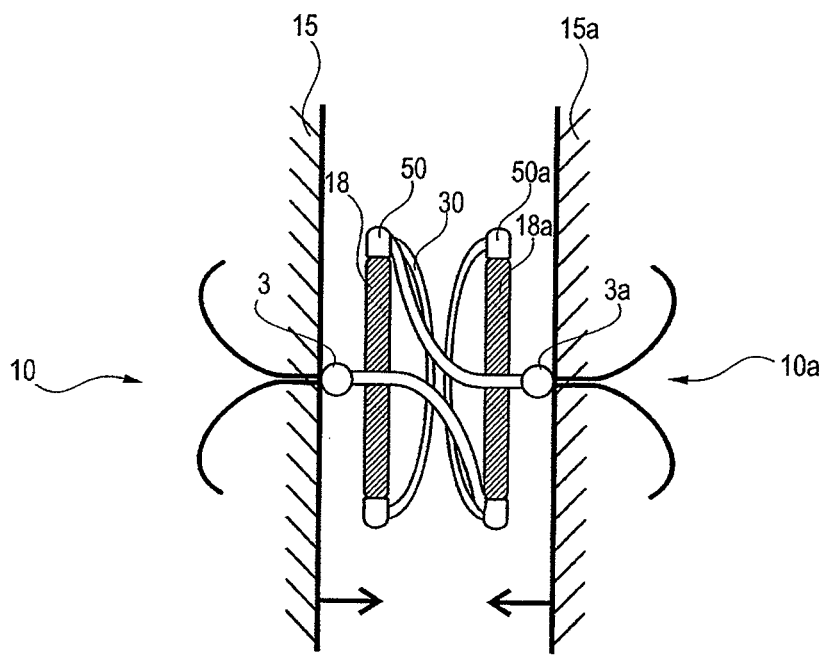
FIG. 37 illustrates the pair of staples of FIG. 36 wherein the thread has cross-hooked the opposing tilt tags and has tightened the tilt tags toward each other so as to draw the two opposing tissue walls toward each to form a gastric stapling.

FIG. 37 illustrates the pair of staples of FIG. 36 wherein the thread 30 has cross-hooked the opposing tilt tags 18, 18a and has tightened the tilt tags 18, 18a toward each other so as to draw the two opposing tissue walls 15, 15a toward each to form a gastric stapling.

While the invention has been described in detail and several embodiments have been illustrated, other embodiments, alternatives, and modifications should become apparent to those skilled in the art without departing from the spirit and scope of the invention.

What is claimed is:

1. A system comprising a surgical thread; and a pair of medical staples, each staple formed from a hyperelastic nickel-titanium alloy wire by bending the wire around itself, the staple having two elongated arms and a central loop, each of the arms normally extending parallel to each other from the loop in a first course, then in two opposing generally semi-circular courses extending upwardly, and outwardly, and downwardly, and terminating in two courses which are perpendicular to the first course, each arm having an end comprising a sharpened endpoint, the arms bendable under resistance and resuming their original position upon release the pair of staples joined by the surgical thread through their respective loops.

2. The system of claim 1 wherein each staple is adapted to easily fold so as to fit within a tube having an internal diameter of about 2 min to 4 mm so as to pass in the working channel of a flexible endoscope and to unfold when pushed out of the tube at a location in a body.

3. The system of claim 1, wherein the arms extend upwardly from the loop first in a parallel direction and then outwardly.

4. The system of claim 1, wherein the endpoints are at least about 0.5 mm above the top of the loop.

5. The system of claim 1 adapted to pleat the cardia of the stomach longitudinally or transversally to treat mild GERD.

6. A system comprising a plurality of pairs of staples according to claim 1 adapted to create an endoscopically placed vertical banding gastroplasty that is reversible by pulling out the staples.

7. The system of claim 1 comprising a plurality of pairs of staples adapted to create an endoscopically placed horizontal gastroplasty that is reversible by pulling out the staples and creating a small reservoir for food at the cardia.

8. The system of claim 1 adapted to reversibly staple a lead of a pace-maker or pace-setter that stimulates the stomach, duodenum and jejunum to contract and help the alimentary bolus in the by-pass tube to progress.

9. The system of claim 1 adapted to attach a probe to a patient's colon.

10. The system of claim 1 wherein each staple is coated with parylene sufficient to protect the staple from attack by gastric fluids and undesirable release of nickel.

11. The system of claim 1 wherein each staple is coated or treated with PTFE sufficient to function as a temperature insulant.

* * * * *